United States Patent [19]

Nakagawa et al.

[11] Patent Number: 5,258,509
[45] Date of Patent: Nov. 2, 1993

[54] PROCESS FOR PRODUCING 2-CARBON-SUBSTITUTED CARBAPENEM DERIVATIVES

[75] Inventors: Susumu Nakagawa; Yoshiaki Kato; Hiroshi Fukatsu, all of Okazaki, Japan

[73] Assignee: Banyu Pharmaceutical Co., Ltd., Tokyo, Japan

[21] Appl. No.: 989,150

[22] Filed: Dec. 11, 1992

Related U.S. Application Data

[63] Continuation of Ser. No. 616,087, Nov. 20, 1990, abandoned.

[30] Foreign Application Priority Data

Nov. 21, 1989 [JP] Japan .................... 1-302529
Apr. 13, 1990 [JP] Japan .................... 2-98597
May 18, 1990 [JP] Japan .................... 2-128446

[51] Int. Cl.$^5$ .................................. C07D 487/04
[52] U.S. Cl. ........................................ 540/302
[58] Field of Search ........................ 540/302, 304

[56] References Cited

U.S. PATENT DOCUMENTS

| | | | |
|---|---|---|---|
| 4,895,940 | 6/1990 | O'Neill et al. | 540/302 |
| 5,025,006 | 6/1991 | DiNinno et al. | 540/302 |
| 5,025,007 | 6/1991 | Greenlee et al. | 540/302 |
| 5,025,008 | 6/1991 | DiNinno et al. | 540/302 |
| 5,037,820 | 8/1991 | DiNinno et al. | 540/302 |

FOREIGN PATENT DOCUMENTS

| | | |
|---|---|---|
| 0010316 | 4/1980 | European Pat. Off. |
| 0265117 | 4/1988 | European Pat. Off. |
| 0330108 | 8/1989 | European Pat. Off. |
| 0444889 | 9/1991 | European Pat. Off. |

OTHER PUBLICATIONS

Solomons, T. W. Graham, Organic Chemistry. N.Y., John Wiley & Sons, 1984, pp. 665–666.
March, Jerry, Advanced Organic Chemistry. N.Y., John Wiley & Sons, 1985, pp. 310–312 and 405–406.
Larock, Richard C. Comprehensive Organic Transformations. N.Y., VCH Publishers, Inc., 1989, p. 58.
Milstein et al. "Palladium–catalyzed ... ", JACS, vol. 101 (17), 1979, pp. 4992–4998.
Sheffy et al. "palladium catalyzed crosscoupling ... " JACS, vol. 105, 1983, pp. 7173–7175.
Stille, John K., "The Palladium–catalyzed cross–coupling Reactions ... " Agnew. Chem. Int. Ed. Engl., vol. 25, 1986, pp. 508–524.
Journal of the American Chemical Society, vol. 108, No. 11, pp. 3033–3040, May 28, 1986, W. J. Scott, et al., "Palladium-Catalyzed Coupling of Vinyl Triflates with Organostannanes. Synthetic and Mechanistic Studies".

Primary Examiner—Richard L. Raymond
Assistant Examiner—John D. Pak
Attorney, Agent, or Firm—Oblon, Spivak, McClelland, Maier & Neustadt

[57] ABSTRACT

A process for producing a 2-(unsubstituted or carbon-substituted)-1-carbapen-2-em-3-carboxylic acid derivative, which comprises reacting a 2-trifluoromethanesulfonyloxy-1-carbapen-2-em-3-carboxylic acid derivative or the 1-carbapen-2-em-3-carboxylic acid derivative derived from a 2-oxo-1-carbapenam-3-carboxylic acid derivative and trifluoromethanesulfonic anhydride, and a stannane derivative in an inert solvent in the presence of a palladium compound and a salt.

16 Claims, No Drawings

PROCESS FOR PRODUCING 2-CARBON-SUBSTITUTED CARBAPENEM DERIVATIVES

This application is a continuation of application Ser. No. 07/616,087, filed on Nov. 20, 1990, now abandoned.

The present invention relates to a novel process for producing 2-(unsubstituted or carbon-substituted)carbapenam derivatives among carbapenem derivatives useful as agents for treating infectious diseases caused by bacteria in the field of pharmaceuticals.

Thienamycin found in nature as a compound having a carbapenem structure has an excellent antibacterial spectrum over a wide range and strong antibacterial activities, and its development as a pharmaceutical has been expected. However, thienamycin is chemically unstable and is likely to be decomposed by a certain enzyme in vivo such as renal dehydropeptidase I (hereinafter referred to simply as DHP-I), and it has not been developed for a practical use. Under these circumstances, various studies have been made to develop better carbapenem derivatives. As a result, imipenem (generic name) has been practically developed for the first time as a pharmaceutical product. Imipenem has better antibacterial activities than thienamycin and has improved chemical stability. However, the stability against DHP-I has not been improved. Therefore, many syntheses and researches are continuously conducted.

Most of the researches for such derivatives are directed to chemical modification of the side chain at the 2-position, and they are researches for the same 2-(substituted thio)carbapenem derivatives as thienamycin and imipenem. At present, a method represented by the following formulas is commonly employed as the synthesis thereof.

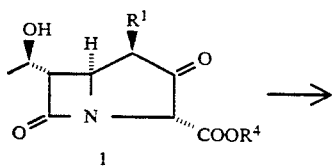

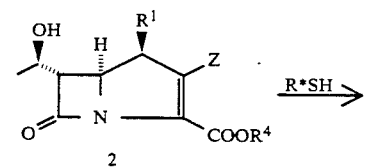

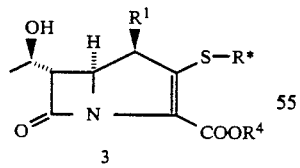

In the above formulas, $R^1$ is a hydrogen atom or a methyl group, $R^4$ is a carboxyl-protecting group, Z is a leaving group, and $R^*$ is the intended side chain.

Namely, using a compound of the formula 1 readily available with its synthesis having been industrially established, as the starting material, an active intermediate of the formula 2 is produced and subjected to a coupling reaction with a thiol having the desired side chain. According to this method, once the thiol compound having the desired side chain has been obtained, it is possible to synthesize a 2-(substituted thio)carbapenem. Thus, this method is excellent in that it is applicable not only for the production of a specific compound but also for researches for derivatives wherein various thio side chains are to be introduced.

Recently, an attention has been drawn to 2-carbon-substituted carbapenem derivatives for their characteristic antibacterial activities and for improvement in the stability against DHP-I. For example, R. Guthikonda et al. disclose 2-arylcarbapenem derivatives in J. Med. Chem., vol. 30, p. 871 (1987), and S. Schmitt et al. have reported 2-(substituted methyl)carbapenem derivatives in J. Antibiotics, vol. 41, p. 780 (1988). However, as is different from the case of the above mentioned 2-(substituted thio)carbapenem derivatives, a process for producing a readily available starting material, has not yet been established.

Further, a cross coupling reaction to form a carbon-carbon bond by means of a palladium catalyst is generally known. For example, reference is made to J.K. Stille Angew. Chem. Int. Ed. Engl., vol. 25, p. 508 (1986). However, it is not reported at all that the aftermentioned enol triflate (a compound of the formula (III)) as a reactive derivative of the compound of the formula (IV) having a carbapenem structure and a stannane derivative of the formula (II) as a carbon-donating agent are reacted by means of a palladium catalyst to form a carbon-carbon bond at the 2-position.

2-carbon-substituted carbapenem derivatives are useful for treating diseases caused by pathogenic bacteria to human and animals. However, there have been various problems in their production. Particularly for the synthesis of their starting compounds, it is required to synthesize them by a multi-stage process as shown by the following formulas according to the above mentioned method of R. Guthikonda et al. such a process is poor in efficiency and is hardly applicable on an industrial scale.

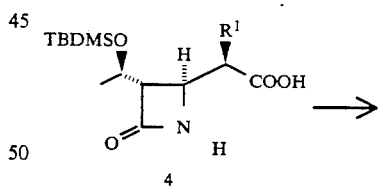

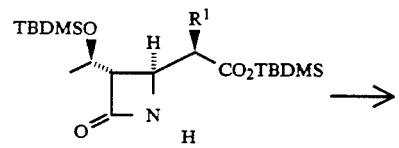

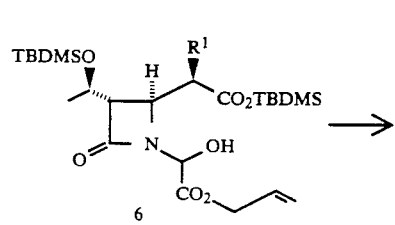

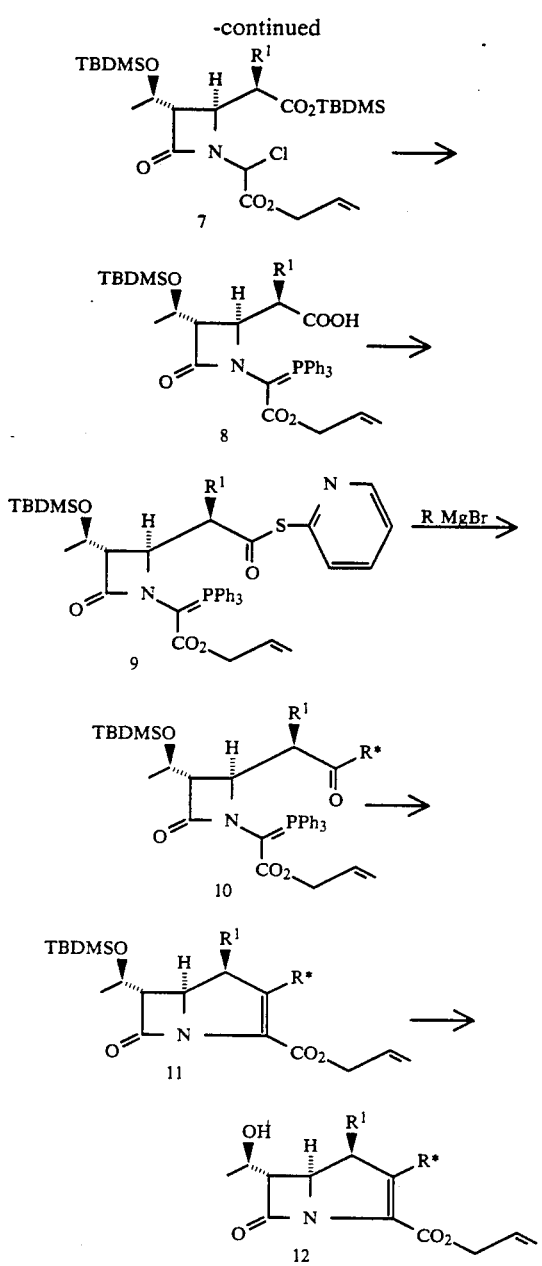

In the above formulas, TBDMS represents a tert-butyldimethylsilyl group, Ph represents a phenyl group, and $R^1$ and $R^*$ are as defined above.

Namely, according to this method, the desired side chain at the 2-position must be introduced prior to forming the carbapenem structure. Accordingly the number of steps has to be increased. Further, there is an additional problem that in order to synthesize the compound of the formula 9 as its starting material, a number of steps are required as shown above.

The present inventors have conducted extensive researches for a process capable of producing readily and by a simple route 2-carbon-substituted carbapenem derivatives showing excellent antibacterial activities against various pathogenic bacteria, using readily available starting materials. As a result, they have found it possible to readily produce such derivatives from compounds of the formula (IV) given hereinafter, for which an industrial method for synthesis has been established, by a cross coupling reaction by means of a palladium catalyst, via a reactive derivative of the formula (III). The present invention has been accomplished on the basis of this discovery. At the same time, the present invention provides a novel process for producing 2-(unsubstituted or carbon-substituted)carbapenem derivatives.

It is an object of the present invention to provide a novel process for producing a 2-carbon-substituted carbapenem readily and by a simple route using a readily available starting material.

The present invention provides a novel process for producing a 2-(unsubstituted or carbon-substituted)-1-carbapen-2-em-3-carboxylic acid derivative, which comprises reacting a 2-trifluoromethanesulfonyloxy-1-carbapen-2-em-3-carboxylic acid derivative or the 1-carbapen-2-em-3-carboxylic acid derivative derived from a 2-oxo-1-carbapenam-3-carboxylic acid derivative and trifluoromethanesulfonic anhydride, and a stannane derivative in an inert solvent in the presence of a palladium compound and a salt.

More particularly, the present invention provides a process for producing a compound of the formula:

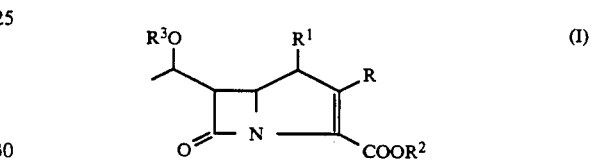

wherein R is a hydrogen atom or an organic residual group, $R^1$ is a hydrogen atom or a methyl group, $R^2$ is a hydrogen atom or a carboxyl-protecting group, and $R^3$ is a hydrogen atom or a hydroxyl-protecting group, which comprises subjecting a compound of the formula:

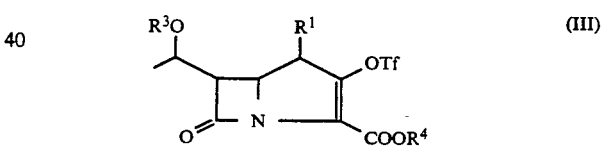

wherein $R^1$ and $R^3$ are as defined above, $R^4$ is a carboxyl-protecting group, and Tf is a trifluoromethanesulfonyl group, or a compound of the formula:

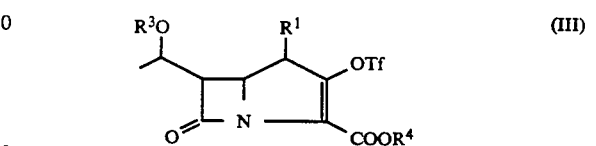

wherein $R^1$, $R^3$, $R^4$ and Tf are as defined above, derived from a compound of the formula:

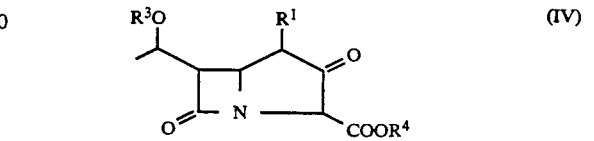

wherein $R^1$, $R^3$ and $R^4$ are as defined above and trifluoromethanesulfonic anhydride, and a compound of the formula:

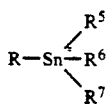
(II)

wherein R is as defined above, and each of $R^5$, $R^6$ and $R^7$ which may be the same or different, is a lower alkyl group, to a coupling reaction in an inert solvent in the presence of a palladium compound and a salt, and, if necessary, removing any protecting group.

Now, various terms used in this specification and preferred embodiments of the present invention will be described.

The carbapenem derivatives of the present invention have optical isomers and steric isomers based on the asymmetrical carbon atoms at the 1-position, 5-position, 6-position and 8-position. The present invention includes all of such isomers. However, particularly preferred among these isomers is a compound of a (5R,6S,8R) configuration i.e. a compound having a steric configuration of (5R,6S) (5,6-trans) like thienamycin and in which the carbon atom at the 8-position takes a R-configuration, or a compound of a (1S,5R,6S,8R) configuration in a case where a methyl group is present at the 1-position.

Accordingly, a group of preferred compounds are represented by the formula:

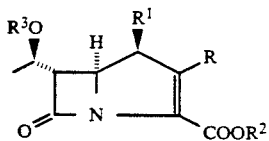
(I')

wherein R, $R^1$, $R^2$ and $R^3$ are as defined above.

A preferred 2-trifluoromethanesulfonyloxy-1-carbapen-2-em-3-carboxylic acid derivative is a compound of the formula:

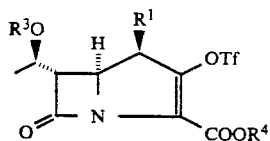
(III)

wherein $R^1$, $R^3$ and $R^4$ are as defined above, which is obtained by reacting a compound of the formula:

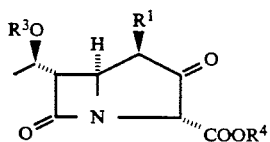
(IV)

wherein $R^1$, $R^3$ and $R^4$ are as defined above, and trifluoromethanesulfonic anhydride. This compound can be produced on an industrial scale, as shown in Example 1.

The term "lower" means that the carbon number of the group modified by this term is from 1 to 6.

The lower alkyl group means an alkyl group such as a methyl group, an ethyl group, a n-propyl group, an isopropyl group, a n-butyl group, an isobutyl group, a sec-butyl group, a tert-butyl group, a n-pentyl group, a n-hexyl group, an isohexyl group, a cyclopropyl group or a cyclobutyl group. An alkyl group having from 1 to 4 carbon atoms such as a methyl group, an ethyl group or a n-butyl group is preferred.

The lower alkenyl group means an alkenyl group such as a vinyl group, a 1-propenyl group, a 1-butenyl group, a 1-pentenyl group or a 1-hexenyl group. An alkenyl group having from 2 to 4 carbon atoms such as a vinyl group, a 1-propenyl group or a 1-butenyl group is preferred.

The lower alkynyl group means an alkynyl group such as an ethynyl group, a 1-propynyl group, a 1-butynyl group, a 1-pentynyl group or a 1-hexynyl group. An alkynyl group having from 2 to 4 carbon atoms such as an ethynyl group, a 1-propynyl group or a 1-butynyl group is preferred.

The aryl group means a phenyl group or a condensed polycyclic hydrocarbon group. A phenyl group or a naphthyl group is preferred.

The non-fused or fused heterocyclic group containing at least one hetero atom selected from the group consisting of a nitrogen atom, an oxygen atom and a sulfur atom, may be saturated or unsaturated, and may be, for example, a pyrrolyl group, an imidazolyl group, a triazolyl group, a tetrazolyl group, a pyrazolyl group, a pyrrolidinyl group, an imidazolidinyl group, a pyrazolidinyl group, a pyrimidinyl group, a pyridyl group, a pyridinio group, a piperidyl group, an indolyl group, a thienyl group, a furanyl group, a thiazolyl group, a thiadiazolyl group or a xanthenyl group.

The organic residual group is a substituent selected from the group consisting of a lower alkyl group, a lower alkenyl group, a lower alkynyl group, an aryl group and a non-fused or fused 5-membered or 6-membered heterocyclic group having at least one hetero atom selected from the group consisting of a nitrogen atom, an oxygen atom and a sulfur atom.

The organic residual group may optionally have a substituent. Specific examples of such substituent include, for example, the following: a halogen atom such as a fluorine atom, a chlorine atom or a bromine atom; a hydroxyl group; a lower alkoxy group such as a methoxy group or an ethoxy group; a carbamoyloxy group such as a carbamoyloxy group, a methylaminocarbonyloxy group, a dimethylaminocarbonyloxy group or a phenylaminocarbonyloxy group; a thio group substituted by the above mentioned lower alkyl group such as a methylthio group or an isopropylthio group; a thio group substituted by the above mentioned hetero ring; a lower alkylthio group substituted by the above mentioned hetero ring; an amino group; a lower alkylamino group such as a methylamino group, an ethylamino group or a dimethylamino group; an amidino group; a guanidino group; an acyl amino group such as an acetylamino group or a propionylamino group; a carboxyl group; an oxycarbonyl group substituted by the above mentioned lower alkyl group such as a methoxycarbonyl group or an ethoxycarbonyl group; an aminocarbonyl group such as an aminocarbonyl group, a methylaminocarbonyl group, an ethylaminocarbonyl group, a dimethylaminocarbonyl group or a pyrrolidinocarbonyl group; a lower alkanoyl group such as an acetyl group or a propionyl group; a cyano group; a sulfo group, a lower alkyl group, a lower alkenyl group, a lower alkynyl group, an aryl group and the above mentioned heterocyclic group. The functional group such as an amino group or a carboxyl group may have a protecting group as the case requires.

The lower alkoxy group is a hydroxyl group substituted by the above mentioned lower alkyl group, and a methoxy group, an ethoxy group, a n-propoxy group or an isopropoxy group is preferred.

The lower alkoxycarbonyl group is an oxycarbonyl group substituted by the above mentioned lower alkyl group, such as a methoxycarbonyl group, an ethoxycarbonyl group, a n-propoxycarbonyl group or a tert-butoxycarbonyl group. Among them, an alkoxycarbonyl group having from 2 to 5 carbon atoms such as a methoxycarbonyl group, an ethoxycarbonyl group or a tert-butoxycarbonyl group is preferred.

The aminocarbonyl group represents in addition to a carbamoyl group, a lower alkylcarbamoyl group, a dilower alkylcarbamoyl group as well as a heterocyclic group obtained when a lower alkyl group of the above mentioned dilower alkylcarbamoyl group forms an alkylene group together with an adjacent nitrogen atom and if necessary, together with a hetero atom such as an oxygen atom, a nitrogen atom or a sulfur atom. Such a heterocyclic group may be, for example, a 1-aziridinyl group, a 1-azetidinyl group, a 1-pyrrolidinyl group, a piperidino group or a morpholino group. Preferred examples of the aminocarbonyl group include, for example, a carbamoyl group, a methylcarbamoyl group, an ethylcarbamoyl group, an isopropylcarbamoyl group, a dimethylcarbamoyl group, a diethylcarbamoyl group, an ethylmethylcarbamoyl group, a 1-pyrrolidinylcarbonyl group and a morpholinocarbonyl group.

The organic residual group may be substituted by at least two above mentioned substituents which may be the same or different.

$R^5$, $R^6$ and $R^7$ may be the same or different and each represents a lower alkyl group. In a preferred embodiment, all of them are the same and n-butyl groups or methyl groups.

The carboxyl-protecting group for $R^2$ or $R^4$ may be a protecting group commonly employed. For example, a lower alkyl group such as a methyl group, an ethyl group or a tert-butyl group; a halogeno lower alkyl group such as a 2-iodoethyl group or a 2,2,2-trichloroethyl group; a lower alkoxymethyl group such as a methoxymethyl group or an ethoxymethyl group; a lower alkoxycarbonyloxy lower alkyl group such as a methoxycarbonyloxymethyl group, an ethoxycarbonyloxymethyl group, a tert-butoxycarbonyloxymethyl group or a 1-ethoxycarbonyloxyethyl group; a lower alkanoyl lower alkyl group such as an acetoxymethyl group, a propionyloxymethyl group, a pivaloyloxymethyl group or a 1-acetoxyethyl group; a (5-methyl-2-oxo-1,3-dioxol-4-yl)methyl group; a phthalidyl group; a lower alkenyl group such as a vinyl group or an allyl group; an aryl lower alkyl group which may have a suitable substituent, such as a benzyl group, a 4-methoxybenzyl group, a 4-nitrobenzyl group, a 2-nitrobenzyl group, a diphenylmethyl group or a trityl group; an aryl group which may have a suitable substituent, such as a phenyl group or a 4-nitrophenyl group; or a lower alkylsilyl group such as a trimethylsilyl group or a tertbutyldimethylsilyl group may be mentioned.

As the amino-protecting group for the substituent of the organic residual group, an aralkylidene group such as a benzylidene group, a 4-chlorobenzylidene group, a 4-nitrobenzylidene group, a salicylidene group, an α-naphthylidene group or a β-naphthylidene group; an aralkyl group such as a benzyl group, a 4-methoxybenzyl group, a 3,4-dimethoxybenzyl group, a 2-nitrobenzyl group, a 4-nitrobenzyl group, a benzhydryl group or a bis (4-methoxyphenyl)methyl group; a lower alkanoyl group such as a formyl group, an acetyl group, a propionyl group, a butylyl group, an oxalyl group, a succinyl group or a pivaloyl group; a halogeno lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tert-butoxycarbonyl group; a halogeno lower alkoxycarbonyl group such as a 2-iodoethyloxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2propenyloxycarbonyl group, a 2-butenyloxycarbonyl group or a cinnamyloxycarbonyl group; an aralkyloxycarbonyl group such as a benzyloxycarbonyl group, a 2-nitrobenzyloxycarbonyl group, a 4-nitrobenzyloxycarbonyl group or a phenethyloxycarbonyl group; or a lower alkylsilyl group such as a trimethylsilyl group or a tert-butyldimethylsilyl group, may be mentioned.

In the reaction of the present invention, the hydroxyl group of the hydroxyethyl group at the 6-position may not necessarily be protected, but may be protected as the case requires. As the hydroxyl-protecting group for $R^3$, a protecting group commonly employed may be used. For example, a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a 4-methoxybenzyl group, a 2,4-dimethoxybenzyl group, a 2-nitrobenzyl group, a 4-nitrobenzyl group or a trityl group; an acyl group such as a formyl group or an acetyl group; a lower alkoxycarbonyl group such as a tert-butoxycarbonyl group, a 2-iodoethyloxycarbonyl group or a 2,2,2-trichloroethyloxycarbonyl group; an alkenyloxycarbonyl group such as a 2-propenyloxycarbonyl group, a 2-chloro-propenyloxycarbonyl group, a 3-methoxycarbonyl-2-propenyloxycarbonyl group, a 2-methyl-2propenyloxycarbonyl group, a 2-butenyloxycarbonyl group or a cinnamyloxycarbonyl group; or an aralkyloxycarbonyl group such as a benzyloxycarbonyl group, a 4-methoxybenzyloxycarbonyl group, a 2-nitrobenzyloxycarbonyl group or a 4-nitrobenzyloxycarbonyl group, may be mentioned.

Now, the process of the present invention will be described.

The 2-(unsubstituted or carbon-substituted)-1-carbapen-2-em-3-carboxylic acid derivative (hereinafter referred to as the desired product) can be produced by subjecting a 2-trifluoromethanesulfonyloxy-1-carbapen-2-em-3-carboxylic acid derivative and a stannane derivative having a side chain (a hydrogen atom or an organic residual group) capable of forming the desired side chain at the 2-position, to a coupling reaction in an inert solvent in the presence of a palladium compound and a salt.

The 2-trifluoromethanesulfonyloxy-1-carbapen-2-em-3-carboxylic acid derivative can be produced by reacting a -oxo-1-carbapenam-3-carboxylic acid derivative and trifluoromethanesulfonic anhydride in an inert solvent. The 2-trifluoromethanesulfonyloxy-1-carbapen-2-em-3-carboxylic acid derivative thus obtained can be used for the reaction with the stannane derivative without isolation or after isolation.

Now, the process for producing the compound of the formula (I) of the present invention will be described in detail.

The compound of the formula (III) can be prepared by reacting the compound of the formula (IV) with from 1 to 2 equivalent of trifluoromethanesulfonic anhydride in the presence of from 1 to 2 equivalent of a base. This reaction is conducted in a commonly employed inert solvent which does not adversely affect the reaction, such as tetrahydrofuran (THF), dioxane, acetone, acetonitrile, chloroform, dichloromethane, ethyl acetate, N,N-dimethylformamide (DMF), or N,N-dimethylacetoamide, or in a solvent mixture thereof. Preferably, THF, dichloromethane or acetonitrile is employed. As the base, an inorganic base such as sodium hydrogen carbonate, potassium carbonate or magnesium carbonate, or an organic base such as triethylamine, diisopropylethylamine, N-methylmorpholine or diisopropylamine, may be mentioned. Preferably, diisopropylethylamine or diisopropylamine is employed. There is no particular restriction as to the reaction temperature and the reaction time. However, the reaction is usually conducted at a temperature of from $-78$ to $+5°$ C. for from 5 minutes to 3 hours. The reaction mixture may be treated in accordance with a usual method to obtain the compound of the formula (III). However, the reaction mixture can be used without any purification for the next reaction.

The compound of the formula (I) of the present invention can be obtained by reacting the compounds of the formula (III) and (II) in the presence of a palladium compound and a salt. As the palladium compound, tetrakis(triphenylphosphine)palladium(O), bis(dibenzylideneacetone)palladium(O), tris(dibenzylideneacetone)dipalladium(O), dichlorobis(triphenylphosphine)palladium(II), dichlorobis(benzonitrile)palladium(II), carbonyltris(triphenylphosphine)palladium(O), transmethylbis(triphenylphosphine)palladium(II) or trans-(4-tert-butylcyclohexen-1-yl)chlorobis(triphenylphosphine)palladium(II) may be mentioned. Preferably, tetrakis(triphenylphosphine)palladium(O), bis(dibenzylideneacetone)palladium(O) or tris(dibenzylideneacetone)dipalladium(O) is employed. As the salt, a lithium halide such as lithium fluoride, lithium chloride, lithium bromide or lithium iodide; a sodium halide such as sodium fluoride or sodium chloride; a potassium halide such as potassium chloride or potassium iodide; a cesium halide such as cesium fluoride or cesium chloride; a zinc halide such as zinc chloride or zinc iodide; or a quaternary ammonium halide such as tetra-n-butylammonium fluoride or tetra-n-butylammonium iodide, may be mentioned. Preferably, lithium chloride or zinc chloride is employed. These salts may be used as a mixture of two or more different types.

The reaction of the present invention may sometimes be accelerated by an addition of a ligand of palladium. As such ligand, tris(2,4,6-trimethoxyphenyl)phosphine, tris(2,6-dimethoxyphenyl)phosphine, tris(4-methoxyphenyl)phosphine, triphenylphosphine, tri(2-furyl)phosphine or tri(2-thienyl)phosphine may, for example, be mentioned. Preferably, tris(2,4,6-trimethoxyphenyl)phosphine or tri(2-furyl)phosphine is employed.

This reaction is conducted in a commonly employed inert solvent which does not adversely affect the reaction, such as THF, dioxane, acetonitrile, 1,2-dimethoxyethane, diglyme, DMF, dimethyl sulfoxide (DMSO), sulforane, N-methylpyrrolidinohe, hexamethylphosphoramide (HMPA), or 1,3-dimethyl-3,4,5,6-tetrahydro-2(1H)-pyrimidinone (DMPU), or a solvent mixture thereof. Preferably, DMF, DMSO, N-methylpyrrolidinone, HMPA or DMPU is employed.

The amounts of the respective reaction reagents to the compound of the formula (III) are not particularly limited. It is usual to employ from 1 to 2 mols of the compound of the formula (II), from 0.001 to 0.05 mol of the palladium compound, from 1 to 5 mols of the salt and, in the case where a ligand of palladium is added, from 0.001 to 0.05 mol of such ligand, per mol of the compound of the formula (III).

There is no particular restriction as to the reaction temperature and the reaction time. However, the reaction is usually conducted at a temperature of from $-20$ to $40°$ C. for from 1 to 48 hours. The reaction mixture is treated in accordance with a usual method to obtain the compound of the formula (I) of the present invention.

The compound of the formula (I) of the present invention may be converted to a carbapenem derivative useful as a pharmaceutical by removing any protecting group, as the case requires. When the carboxyl-protecting group for $R^2$ is a protecting group readily hydrolyzable in vivo, such as an acetoxymethyl group, a pivaloyloxymethyl group, a (5-methyl-2-oxo-1,3-dioxol-4-yl)methyl group or a phthalidyl group, no removal of such protecting group is required, and the product can be used as a drug for oral administration.

The reaction for the removal of a protecting group can be conducted by a method per se known depending upon the type of the protecting group.

The compound of the formula (I) can be converted by a usual method to a pharmaceutically acceptable salt or ester thereof.

Further, among the compounds of the formula (I), compounds of the formula (I-a):

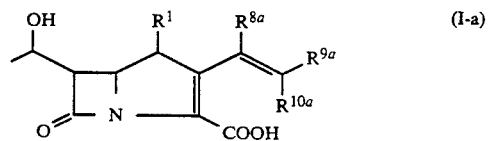

wherein $R^1$ is a hydrogen atom or a methyl group, and each of $R^{8a}$, $R^{9a}$ and $R^{10a}$ is a substituent selected from the group consisting of a hydrogen atom, a lower alkyl group, an aminocarbonyl group, a lower alkoxy group, a cyano group, a lower alkoxycarbonyl group and a nitro group, or pharmaceutically acceptable salts or esters thereof, are novel compounds, and they have excellent antibacterial activities and thus are useful as antibacterial agents. The compounds of the formula (I-a) may generally be classified into compounds of the formula (I-b):

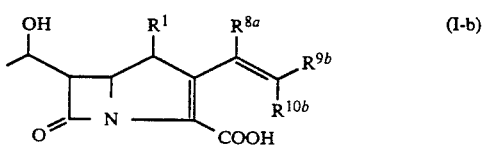

wherein $R^1$ is a hydrogen atom or a methyl group, and each of $R^{8b}$, $R^{9b}$ and $R^{10b}$ is a hydrogen atom or a lower alkyl group, or pharmaceutically acceptable salts or esters thereof, and compounds of the formula (I-c):

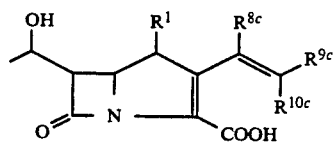

(I-c)

wherein $R^1$ is a hydrogen atom or a methyl group, and each of $R^{8c}$, $R^{9c}$ and $R^{10c}$ is a substituent selected from the group consisting of a hydrogen atom, a lower alkyl group, an aminocarbonyl group, a lower alkoxy group, a cyano group, a lower alkoxycarbonyl group and a nitro group, provided $R^{8c}$, $R^{9c}$ and $R^{10c}$ are not simultaneously hydrogen atoms or lower alkyl groups, or pharmaceutically acceptable salts or esters thereof. Among them, compounds of the formula (I-b) are preferred.

The compound of the formula (I-a) can be prepared by subjecting a compound of the formula:

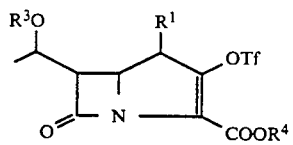

(III)

wherein $R^1$ is a hydrogen atom or a methyl group, $R^3$ is a hydrogen atom or a hydroxyl-protecting group, $R^4$ is a carboxyl-protecting group, and Tf is a trifluoromethanesulfonyl group, and a compound of the formula:

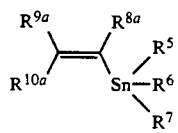

(II-a)

wherein each of $R^5$, $R^6$ and $R^7$ is a lower alkyl group, and each of $R^{8a}$, $R^{9a}$ and $R^{10a}$ is a substituent selected from the group consisting of a hydrogen atom, a lower alkyl group, an aminocarbonyl group, a lower alkoxy group, a cyano group, a lower alkoxycarbonyl group and a nitro group, to a coupling reaction in the presence of a palladium compound and a salt, and then removing any protecting group, as the case requires, or by reacting a compound of the formula:

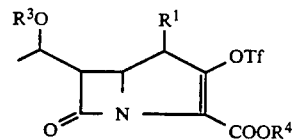

(III)

wherein Tf is a trifluoromethanesulfonyl group, $R^1$ is a hydrogen atom or a methyl group, $R^3$ is a hydrogen atom or a hydroxyl-protecting group and $R^4$ is a carboxyl-protecting group, derived from a compound of the formula:

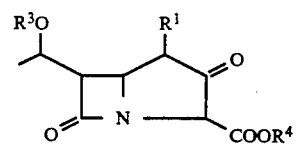

(IV)

wherein $R^1$, $R^3$ and $R^4$ are as defined above and trifluoromethanesulfonic anhydride, and a compound of the formula:

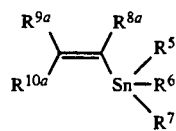

(II-a)

wherein each of $R^5$, $r^6$ and $R^7$ is a lower alkyl group, and each of $R^{8a}$, $R^{9a}$ and $R^{10a}$ is a substituent selected from the group consisting of a hydrogen atom, a lower alkyl group, an aminocarbonyl group, a lower alkoxy group, a cyano group, a lower alkoxycarbonyl group and a nitro group, in the presence of a palladium compound and a salt, and then removing any protecting group as the case requires. The preparation of the compound of the formula (I-a) can be conducted in the same manner as the production of the compound on the formula (I).

Specific compounds of the formula (I-a) have the following side chains as the side chain at the 2-position of the carbapenem structure:

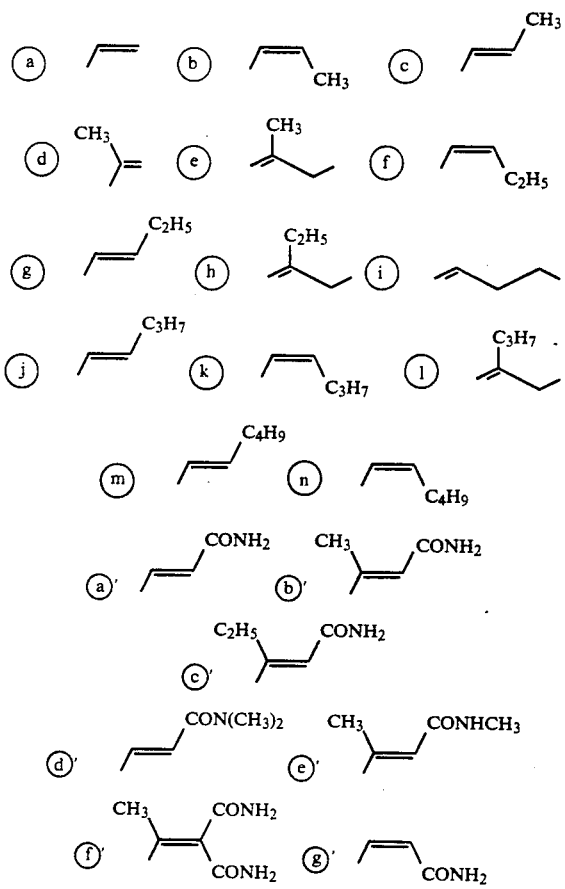

-continued

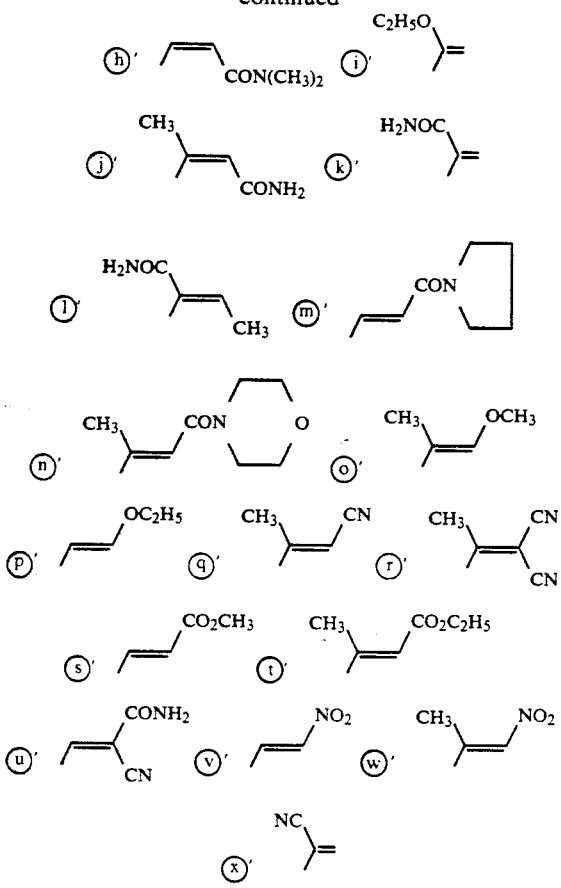

Now, specific examples of the compound of the formula (I) will be given below:

(1) (5R,6S)-6-[(1R)-1-hydroxyethyl]-2-vinyl-1-carbapen-2-em-3-carboxylic acid (compound with side chain (a))
(2) (1S,5R,6S)-6-[(1R)-1-hydroxyethyl]-2-vinyl-1-methylcarbapen-2-em-3-carboxylic acid (compound with side chain (a))
(3) (5R,6S)-6-[(1R)-1-hydroxyethyl]-2-(1-methylvinyl)-1-carbapen-2-em-3-carboxylic acid (compound with side chain (b) or (c))
(4) (1S,5R,6S)-6-[(1R)-1-hydroxyethyl]-2-(1-methylvinyl)-1-methylcarbapen -2-em-3-carboxylic acid (compound with side chain (b) or (c))
(5) (5R,6S)-2-(1-ethylvinyl)-6-[(1R)-1-hydroxyethyl]-1-carbapen-2-em-3-carboxylic acid (compound with side chain (f) or (g))
(6) (1S,5R,6S)-2-(1-ethylvinyl)-6-[(1R)-1hydroxyethyl]-1-methylcarbapen-2-em-3-carboxylic acid (compound with side chain (f) or (g))
(7) (5R,6S)-6-[(1R)-1-hydroxyethyl]-2-(1-propylvinyl) -1-carbapen-2-em-3-carboxylic acid (compound with side chain (j) or (k))
(8) (1S,5R,6S)-6-[(1R)-1-hydroxyethyl]-2-(1-propylvinyl) -1-methylcarbapen-2-em-3-carboxylic acid (compound with side chain (j) or (k))
(9) (5R,6S)-2-[(E)-2-carbamoylvinyl]-6-[(1R)-1-hydroxyethyl] -1-carbapen-2-em-3-carboxylic acid (compound with side chain (a)')
(10) (1S,5R,6S)-2-[(E)-2-carbamoylvinyl]-6-[(1R)-1hydroxyethyl]-1-methylcarbapen-2-em-3-carboxylic acid (compound with side chain (a)')
(11) (5R,6S)-2-[(E)-2-dimethylcarbamoylvinyl]-6-[(1R)-1-hydroxyethyl]-1-carbapen-2-em-3-carboxylic acid (compound with side chain (g)')
(12) (1S,5R,6S)-2-[(E)-2-dimethylcarbamoylvinyl]-6[(1R)-1-hydroxyethyl]-1-methylcarbapen-2-em-3-carboxylic acid (compound with side chain (d)')
(13) (5R,6S)-2-[(Z)-2-carbamoylvinyl]-6-[(1R)-1hydroxyethyl]-1-carbapen-2-em-3-carboxylic acid (compound with side chain (g)')
(14) (1S,5R,6S)-2-[(Z)-2 carbamoylvinyl]-6-[(1R)-1hydroxyethyl]-1-methylcarbapen-2-em-3-carboxylic acid (compound with side chain (g)')
(15) (5R,6S)-2-[(Z)-2-dimethylcarbamoylvinyl]-6-](1R)-1-hydroxyethyl]-1-carbapen-2-em-3-carboxylic acid (compound with side chain (h)')
(16) (1S 5R 6S)-2-[(Z)-2-dimethylcarbamoylvinyl]-6-[(1R) -1-hydroxyethyl]-1-methylcarbapen-2-em-3-carboxylic acid (compound with side chain (h)')
(17) (5R,6S)-2-(1-ethoxyvinyl)-6-[(1R)-1hydroxyethyl]-1-carbapen-2-em-3-carboxylic acid (compound with side chain (i)')
(18) (1S,5R,6S)-2-(1-ethoxyvinyl)-6-[(1R)-1-hydroxyethyl] -1-methylcarbapen-2-em-3-carboxylic acid (compound with side chain (i)')
(19) (5R,6S)-2-(1-carbamoylvinyl)-6-[(1R)-1hydroxyethyl]-1-carbapen-2-em-3-carboxylic acid (compound with side chain (k)')
(20) (1S,5R,6S)-2-(1-carbamoylvinyl)-6-[(1R)-1hydroxyethyl]-1-methylcarbapen-2-em-3-carboxylic acid (compound with side chain (k)')
(21) (5R,6S)-2-[(E)-2-ethoxyvinyl]-6-[(1R)-1hydroxyethyl]-1-carbapen-2-em-3-carboxylic acid (compound with side chain (p)')
(22) (1S,5R,6S)-2-[(E)-2-ethoxyvinyl]-6-[(1R)-1hydroxyethyl]-1-methylcarbapen-2-em-3-carboxylic acid (compound with side chain (p)')
(23) (5R,6S)-2-(2,2-dicyano-1-methylvinyl)-6[(1R)-1-hydroxyethyl]-1-carbapen-2-em-3-carboxylic acid (compound with side chain (r)')
(24) (1S,5R,6S)-2-(2,2-dicyano-1-methylvinyl)-6-[(1R) -1-hydroxyethyl]-1-methylcarbapen-2-em-3-carboxylic acid (compound with side chain (r)')
(25) (5R,6S)-6-[(1R)-1-hydroxyethyl]-2-[(E)-2-nitrovinyl]-1-carbapen-2-em-3-carboxylic acid (compound with side chain (v)')
(26) (1S,5R,6S)-6-[(1R)-1-hydroxyethyl]-2-[(E)-2-nitrovinyl]-1-methylcarbapen-2-em-3-carboxylic acid (compound with side chain (v)')
(27) (5R,6S)-2-(1-cyanovinyl)-6-[(1R)-1-hydroxyethyl] -1-carbapen-2-em-3-carboxylic acid (compound with side chain (x)')
(28) (1S,5R,6S)-2-(1-cyanovinyl)-6-[(1R)-1hydroxyethyl]-1-methylcarbapen-2-em-3-carboxylic acid (compound with side chain (x)')

Among these compounds, E-isomer such as compounds (3), (4), (9), (10), (11) and (12) are preferred.

Among preferred compounds of the formula (I-b), more preferred compounds are those having a terminal vinyl group as the side chain at the 2-position of the carbapenem structure, wherein $R^{9b}$ and $R^{10b}$ are hydrogen atoms.

The compounds of the formula (I-a) can be converted by usual methods to pharmaceutically acceptable non-toxic salts or esters thereof.

The non-toxic salts of the compounds of the formula (I-a) mean pharmaceutically acceptable common salts and mean salts of the carboxyl group at the 3-position of the carbapenem structure. For example, a salt with an alkali metal such as sodium, potassium or lithium; a salt with an alkaline earth metal such as calcium or magnesium; a salt with an organic amine such as N,N-dibenzylethylenediamine, ethanblamine or triethylamine; or a salt with an amino acid such as aspartic acid, glutamic acid or lysine, may be mentioned.

The non-toxic esters of the compounds of the formula (I-a) mean pharmaceutically acceptable common esters of the carboxyl group at the 3-position of the carbapenem structure. For example, an ester with an alkanoyloxymethyl group such as an acetoxymethyl group or a pivaloyloxymethyl group; an ester with an alkoxycarbonyloxyalkyl group such as a 1-(ethoxycarbonyloxy)ethyl group; an ester with a phthalidyl group; or an ester with a 5-substituted-2-oxo-1,3-dioxol-4-ylmethyl group such as a 5-methyl-2-oxo-1,3-dioxol-4-ylmethyl group, may be mentioned.

The compounds of the formula (I) of the present invention may be converted to pharmaceutically useful carbapenem derivatives by removing a protecting group, as the case requires. When the carboxyl-protecting group for $R^4$ is a protecting group readily hydrolyzable in vivo, such as an acetoxymethyl group, a pivaloyloxymethyl group, a (5-methyl-2-oxo-1,3-dioxol-4-yl)methyl group or a phthalidyl group, such compound can be used as a pharmaceutical for oral administration without removal of such a protecting group.

The reaction for the removal of a protecting group can be conducted by a usual method such as by solvolysis, by reduction by means of a metal or by catalytic reduction, per se known.

For example, a 4-nitrobenzyl group or a 2,2,2-trichloroethyl group may be removed by mild reduction by means of iron or zinc. For example, a 4-methoxybenzyl group, a tert-butyl group or a diphenylmethyl group can be removed by aluminum chloride-anisole. An allyl group can be removed by means of a catalyst composed of a mixture of a palladium compound and triphenylphosphine. For example, a 4-nitrobenzyl group, a benzyl group or a diphenylmethyl group can be removed by catalytic reduction in the presence of a palladium-carbon catalyst. A 2-trimethylsilylethyl group can be removed by tetrabutylammonium fluoride. A 2-nitrobenzyl group can be removed by photolysis.

The compound of the formula (I) can be converted by usual methods to pharmaceutically acceptable salts or esters.

The starting material of the formula (IV) is an important intermediate for the preparation of carbapenem derivatives, and many excellent methods for its preparation have been reported by now. Therefore, they are readily available. For example, reference is made to D.G. Melillo et al., J. Org. Chem., vol. 51, p. 1,498 (1986); L.M. Fuentes et al., J. Am. Chem. Soc., vol. 108, p. 4,675 (1986); R. Deziel et al., Tetrahedron Lett., vol. 30, p. 1,345 (1989) and literatures cited in these reports.

The stannane compound of the formula (II) as the other starting material is either commercially available or can be synthesized in accordance with the general description by J.K. Stille cited above, or literatures cited in the report by M. Pereyere et al., Tin in Organic Synthesis, Butterworths, 1987.

The compounds of the formula (I) or their salts or esters of the present invention exhibit excellent antibacterial activities, and they are new compounds useful as pharmaceuticals and can be used for treatment and prevention of infectious diseases caused by bacteria, such as infectious diseases of respiratory system, infectious diseases of urinary tract, suppurative diseases or surgical infectious diseases.

To specifically demonstrate the usefulness of the compounds of the present invention, the biological test results with respect to the representative compounds are shown below. As is evident from the results, the compounds of the present invention represented by the formula (I-a) are useful as antibiotics, particularly as the ones for oral administration.

(1) Antibacterial activities in vitro

Test method:

The antibacterial activities were measured by the following agar plate dilution method.

One platinum loopful of each test microorganism incubated overnight in Mueller Hinton broth, was inoculated to Mueller Hinton-agar (inoculum size: $10^6$ CFU/ml). Such a culture medium contained a test compound in a predetermined concentration. After incubation at 37° C. for 16 hours, the minimum inhibitory concentration (MIC) was measured and presented by a unit of μg/ml.

Test results:

| Test microorganism | MIC (μg/ml) Compound of Example 25 |
|---|---|
| S. aureus 209P NIHJ JC1 | 0.05 |

(2) Protective effects against experimental infectious disease of mice

Test animal:

Male mice (ddY) of 4 weeks old having body weights of 20±1 g were employed, and the test was conducted with eight mice per group.

Microorganism used:

S. aureus 4970

Test method:

$5 \times 10^5$ cells of the pathogenic microorganism suspended in 5% mucin were intracelially injected to each mouse. One hour after the inoculation of the microorganism, the compound of the present invention was orally administered in the form of solutions having various concentrations. Four days later, the mortality of the mice was determined, and the $ED_{50}$ value was calculated.

Test results:

Compound of Example 25: $ED_{50}$ 0.34 mg/kg

Compound of Example 26: $ED_{50}$ 0.36 mg/kg (3) Concentration in blood and recovery rate in urine Test animal:

ddY male mice of 4 weeks old

Test method:

40 mg/kg of the test compound was orally administered to each mouse, and the change with time of the concentration in blood and the recovery rate in urine for from 0 to 6 hours were measured. The quantitative analysis was conducted by a bioassay using S. lutea PC 11001 as the test microorgansim. With respect to the compound of Example 26, the quantitative analysis was conducted in the form of its non-ester form i.e. as the compound of Example 25.

Test results:

| Compound | Concentration in blood (μg/ml) | | | Recovery rate in urine (%) 0-6 hrs |
|---|---|---|---|---|
| | 0.25 hr later | 0.5 hr later | 1 hr later | |
| Compound of | 4.1 | 2.9 | 1.6 | 1.8 |

-continued

| | Concentration in blood (μg/ml) | | | Recovery rate |
|---|---|---|---|---|
| Compound | 0.25 hr later | 0.5 hr later | 1 hr later | in urine (%) 0–6 hrs |
| Example 25 Compound of Example 26 | 44.9 | 29.1 | 10.2 | 29.7 |

To administer the compound of the present invention for the purpose of treatment, it may be administered in the form of a commonly employed formulation containing the compound of the present invention as the main component and having a pharmaceutically acceptable organic or inorganic solid or liquid carrier suitable for the particular administration method added. With respect to the administration method and the formulation, oral administration in the form of tablets, powders, capsules or syrups, or non-oral administration by intravenous or intramuscular injection or by suppositories, may be employed. Such formulations may be prepared by usual methods commonly employed in this field, and such formulations may contain additives commonly employed such as an adjuvant, a stabilizer, an emulsifier, a wetting agent, a binder or an excipient. The dose is determined by taking into accounts the age, the sex, the body weight, the sensitivity, the administration method, the time and interval for the administration, the degree of the disease, the condition of the patient, the nature of the drug formulation, the type of the formulation and the type of the active ingredient. Usually, the dose is within a range of from 1 to 100 mg/kg per day. It is preferred that a daily dose of from 5 to 30 mg/kg is divided into from 2 to 4 administrations.

EXAMPLES

The present invention is now illustrated in greater detail by way of Examples, but it should not be understood that the present invention is deemed to be limited thereto.

Silica gel for column chromatography used herein is Wakogel® C-300 (Wakojunyaku), and the reverse phase silica gel for column chromatography is LC-SORB® SP-B-ODS (Chemco). Abbreviations used herein have the following meanings.

Me : methyl group
Et : ethyl group
Bu : n-butyl group
Ph : phenyl group
Tf : trifluoromethanesulfonyl group
PMB: 4-methoxybenzyl group
PNB: 4-nitrobenzyl group
POM: pivaloyloxymethyl group
MOPS: 3-morpholinopropanesulfonate

EXAMPLE 1

1) 4-Nitrobenzyl (5R,6S)-6-((1R)-1-hydroxyethyl)-2-trifluoromethanesulfonyloxy -1-carbapen-2-em-3-carboxylate

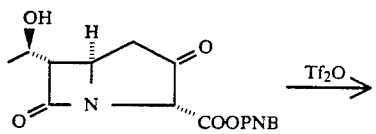

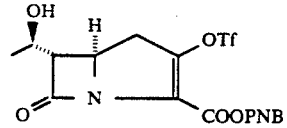

Under a nitrogen atmosphere, to a solution of 128 mg (0.368 mmol) of 4-nitrobenzyl (3R,5R,6S)-6-((1R)-1-hydroxyethyl) -2-oxo-1-carbapenam-3-carboxylate in acetonitrile (3 ml) was added 0.065 ml (0.37 mmol) of diisopropylethylamine at −45° C., followed by 0.062 ml (0.37 mmol) of trifluoromethanesulfonic anhydride, and the mixture was stirred for 2 hours at the same temperature. To the reaction mixture was added ethyl acetate (3 ml), and the organic layer was washed with saturated aqueous sodium bicarbonate followed by saturated aqueous sodium chloride. After the extract was dried over anhydrous magnesium sulfate, the solvent was removed. The residue was purified by silica gel column chromatography (elution with ethyl acetate-hexane system) to give 94.6 mg (yield: 53.6%) of the title compound as a viscous oil.

IR(KBr)cm⁻¹: 1790, 1730, 1520, 1430, 1345, 1220, 1135.

NMR(CDCl₃)δ: 1.35(3H,d,J=6Hz), 3.22(2H,d,J=9Hz), 3.38(1H.dd,J=3&7Hz), 4.20–4.40(2H,m), 5.34&5.50(2H,ABq,J=13Hz), 7.63(2H,d,J=9Hz), 8.25(2H,d,J=9Hz)

2) 4-nitrobenzyl (5R,6S)-6-((1R)-1-hydroxyethyl)-2-(2-propenyl) -1-carbapen-2-em-3-carboxylate

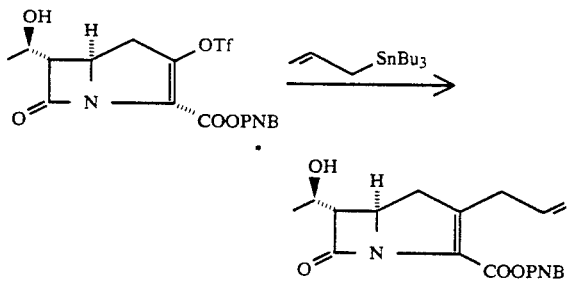

Under a nitrogen atmosphere, 92.6 mg (0.193 mmol) of the compound obtained in Example 1—1), 59.3 mg (0.436 mmol) of zinc chloride, 2.8 mg (0.0049 mmol) of bis(benzylideneacetone)palladium(0), and 2.3 mg (0.0099 mmol) of tri(2-furyl)phosphine was added 75.5 mg (0.228 mmol) of allyl(tri-n-butyl)tin in N-methylpyrrolidinone (3 ml), and the mixture was stirred overnight at room temperature. To the reaction mixture was added 30 ml of ethyl acetate, and the organic layer was washed with water (50 ml×2) followed by saturated aqueous sodium chloride. After the extract was dried over anhydrous magnesium sulfate, and the solvent was removed. The residue was purified by silica gel column chromatography (elution with ethyl acetate-hexane system) to give 49.5 mg (yield: 68.7%) of the title compound as a colorless crystal.

UV(CHCl₃)λmax: 274 nm (ε=14,400).
IR(KBr)cm⁻¹: 1770, 1700, 1520, 1345, 1290.
NMR(CDCl₃) δ: 1.34(3H,d,J=6Hz), 2.89(2H,dd,J=5&9Hz), 3.16(1H,dd,J=3&7Hz), 3.38(2H,br-t,J=8Hz)

EXAMPLE 2

4-Nitrobenzyl (5R,6S)-6-((1R)-1-hydroxyethyl)-2-vinyl-1-carbapen-2-em-3-carboxylate

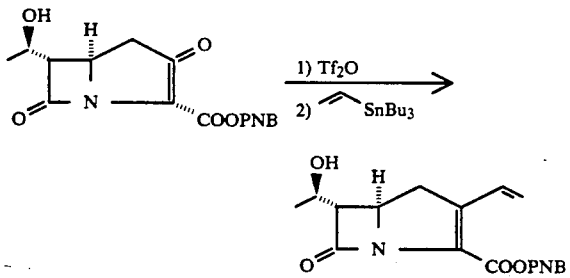

Under a nitrogen atmosphere, to a solution of 128 mg (0.368 mmol) of 4-nitrobenzyl (5R,6S)-6-((1R)-1-hydroxyethyl) -2-oxo-1-carbapenam-3-carboxylate in acetonitrile (3 ml), followed by 0.065 ml (0.37 mmol) of diisopropylethylamine at −45° C., followed by 0.062 ml (0.37 mmol) of trifluoromethanesulfonic anhydride, and the mixture was stirred for 2 hours at the same temperature. To the reaction mixture was added ethyl acetate (3 ml), and the organic layer was washed with saturated aqueous sodium bicarbonate followed by saturated aqueous sodium chloride. After the extract was dried over anhydrous magnesium sulfate, the solvent was removed. The residual triflate was used the next reaction without purification. To 181 mg of this crude product was added 108 mg (0.79 mmol) of zinc chloride, 5.1 mg (0.0087 mmol) of bis(benzylideneacetone)-palladium(0), and 4.2 mg (0.018 mmol) of tri(2-furyl)phosphine was added a solution of 132 mg (0.416 mmol) of vinyl(-tri-n-butyl)tin in N-methylpyrrolidinone (6 ml), and the mixture was stirred for 2 hours at room temperature. To the reaction mixture was added ethyl acetate, and the organic layer was washed with water followed by saturated aqueous sodium chloride. After the extract was dried over anhydrous magnesium sulfate, the solvent was removed. The residue was purified by silica gel column chromatography (elution with ethyl acetate-hexane system) to give 60.3 mg (yield: 47.9%) of the title compound.

UV(CHCl$_3$)λmax: 268 nm ($\epsilon$=12,100), 311 nm ($\epsilon$=11,900).

IR(KBr)cm$^{-1}$: 1760, 1710, 1520, 1340.

NMR(CDCl$_3$) δ: 1.37(3H,d,J=6Hz), 3.06(1H,d,J=10Hz), 3.12(1H,d,J=10Hz), 3.22(1H,dd,J=3&7Hz), 4.10–4.40(2H,m), 5.28&5.53(2H,ABq,J=14Hz), 5.45(1H,d,J=17Hz), 5.52(1H,d,J=11Hz), 7.43(1H,dd,J=11&17Hz), 7.67(2H,d,J=9Hz), 8.25(2H,d,J=9Hz).

EXAMPLE 3

4-Nitrobenzyl (5R,6S)-6-((1R)-1-hydroxyethyl)-2-vinyl-1-carbapen-2-em-3-carboxylate To the crude product of the triflate obtained in the same manner as in Example 2 was added 113 mg (0.83 mmol) of zinc chloride and 9.2 mg (0.0074 mmol) of tetrakis(triphenylphosphine)palladium(0). Under a nitrogen atmosphere, to the mixture was added 138 mg (0.435 mmol) of vinyl(tri-n-butyl)tin in N-methylpyrrolidinone (6 ml), and the mixture was stirred overnight at room temperature. Subsequent operation was carried out in the same manner as in Example 2, and 42.2 mg (yield: 32.0%) of the title compound was obtained. IR and NMR data of this product agreed with those of the compound prepared in Example 2.

EXAMPLE 4

4-Nitrobenzyl (1S,5R,6S)-6-((1R)-1-hydroxyethyl)-2-vinyl-1-methylcarbapen -2-em-3-carboxylate

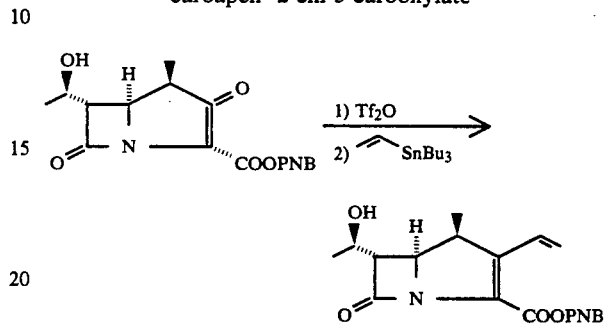

41.7 mg (yield: 30.5%) of the title compound was obtained from 133 mg of 4-nitrobenzyl (1R,3R,5R,6S)-6-((1R) -1-hydroxyethyl)-1-methyl-2-oxo-1-carbapenam-3carboxylate and 138 mg of vinyl(tri-n-butyl)tin in the same manner as in Example 2.

IR(KBr)cm$^{-1}$: 1750, 1710, 1520, 1340, 1300.

NMR(CDCl$_3$) δ: 1.24(3H,d,J=7Hz), 1.37(3H,d,J=6Hz), 3.30(1H,dd,J=3&7Hz), 3.48(1H,m), 4.16-4.38(2H,m), 5.28&5.52(2H,ABq,J=14Hz), 5.54(1H,d,J=11Hz), 5.61(1H,d,J=18Hz), 7.38(1H,dd,J=11&17Hz), 7.69(2H,d,J=8Hz), 8.25(2H,d,J=8Hz).

EXAMPLE 5

4-Methoxybenzyl (1S,5R,6S)6-((1R)-1-hydroxyethyl)-2-vinyl -1-methylcarbapen-2-em-3-carboxylate

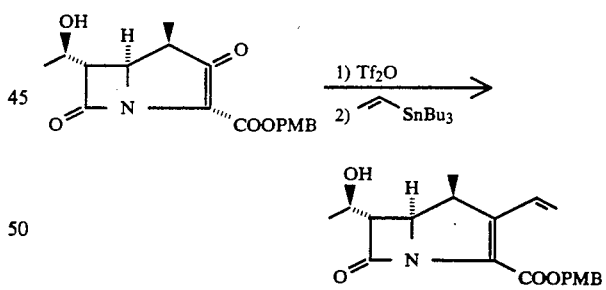

Under a nitrogen atmosphere, to a solution of 128 mg (0.368 mmol) of 4-methoxybenzy-1 (1R,3R,5R,6S)-6-((1R)-1-hydroxyethyl) -1-methyl-2-oxo-1 carbapenam-3-carboxylate in acetonitrile (3 ml) was added 0.065 ml (0.37 mmol) of diisopropylethylamine at −45° C., followed by 0.062 ml (0.37 mmol) of trifluoromethanesulfonic anhydride, and the reaction mixture was stirred for 2 hours at the same temperature. To the reaction mixture was added ethyl acetate, and the organic layer was washed with saturated aqueous sodium bicarbonate followed by saturated aqueous sodium chloride. After the extract was dried over anhydrous magnesium sulfate, the solvent was removed. Under a nitrogen atmosphere, to a solution of 113 mg (0.83 mmol) of zinc chloride, 5.3 mg (0.0091 mmol) of bis(dibenzylideneacetone)palladium(0) and 4.4 mg (0.0185 mmol) of tri(2-furyl)phosphine in N-methylpyrrolidinone (3ml) was added a solution of the residual triflate and 132 mg (0.416 mmol) of vinyl(tri-n-butyl)tin in N-methylpyrrolidinone (3 ml) at −20° C., and the mixture was stirred for 2 hours at room temperature. To the reaction mixture was added ethyl acetate, and the organic layer was washed with water followed by saturated aqueous sodium chloride. After the extract was dried over anhydrous magnesium sulfate, the solvent was removed. The residue was purified by silica gel column chromatography (elution with ethyl acetate-hexane system) to give 35.5 mg (yield: 27%) of the title compound.

IR(KBr)cm$^{-1}$: 1760, 1615, 1520,
NMR(CDCl$_3$) δ: 1.20(3H,d,J=6Hz), 1.36(3H,d,J=6Hz), 3.24(1H,dd,J=3&7Hz), 3.42(1H,m), 4.00–4.30(2H,m), 5.21&5.30(2H,ABq,J=12Hz), 5.46(1H,d,J=11Hz), 5.53(1H,d,J=17Hz), 6.90(2H,d,J=9Hz), 7.35(1H,dd,J=11&17Hz), 7.42(2H,d,J=9Hz)

EXAMPLE 6

4-Nitrobenzyl (5R,6S)-2-(cyclohepten-1-yl)-6-((1R)-1-hydroxyethyl) -1-carbapen-2-em-3-carboxylate

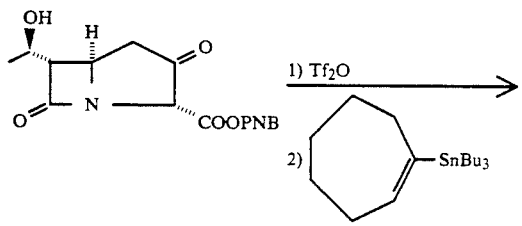

Under a nitrogen atmosphere, to a solution of 348 mg (1 mmol) of 4-nitrobenzyl (3R,5R,6S)-6-((1R)-1-hydroxyethyl) -2-oxo-1-carbapenam-3-carboxylate in THF (5 ml) was added 0.154 ml (1.1 mmol) of diisopropylamine at −78° C., and the mixture was stirred for 10 minutes. To the mixture was added 0.189 ml (1.08 mmol) of trifluoroacetic anhydride at the same temperature. After 15 minutes, to the mixture was added 5 ml of N-methylpyrrolidinone followed by 20.7 mg of tris(-dibenzylideneacetone)dipalladium-chloroform, 42.5 mg (0.08 mmol) of tris(2,4,6-trimethoxyphenyl)phosphine, a solution of 389 mg (1.01 mmol) of cyclohepten-1-yl(tri-n-butyl)tin in N-methylpyrrolidinone (1 ml) and a solution of 225 mg (1.66 mmol) of N-methylpyrrolidinone (2 ml). The −78° C. bath was removed and the reaction mixture quickly raised to ambient temperature using a lukewarm water bath, and the mixture was stirred overnight at room temperature. The reaction mixture was poured into ethyl ether and the organic layer was washed with water followed by saturated aqueous sodium chloride. After the extract was dried over anhydrous magnesium sulfate, the solvent was removed. The residue was purified by silica gel column chromatography (elution with ethyl acetatehexane system) to give 148 mg (yield: 34.7%) of the title compound.

IR(KBr)cm$^{-1}$: 1765, 1730, 1600, 1440, 1340.
NMR(CDCl$_3$) δ: 1.36(3H,d,J=6Hz), 1.40–1.82(6H,m), 2.14–2.34(4H,m), 3.04(2H,m), 3.18(1H,dd,J=3&7Hz), 4.04–4.34(2H,m), 5.26&5.45(2H,ABq,J=14Hz), 6.00(1H,t,J=8Hz), 7.64(2H,d,J=9Hz), 8.24(2H,d,J=9Hz)

EXAMPLE 7

4-Nitrobenzyl (1S,5R,6S)-2-(cyclohepten-1-yl)-6-((1R)-1-hydroxyethyl) -1-methylcarbapen-2-em-3-carboxylate

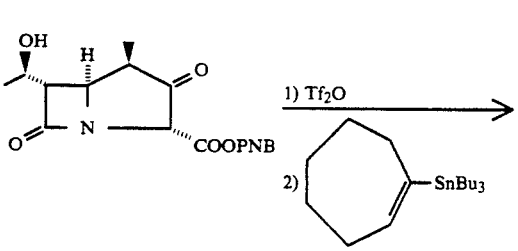

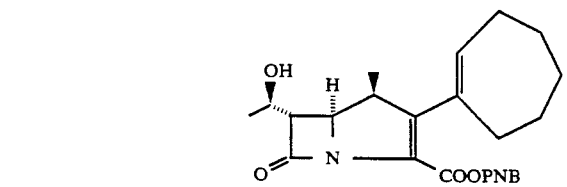

169 mg (yield: 38.4%) of the title compound was obtained from 362 mg of 4-nitrobenzyl (1R,3R,5R,6S)-6-((1R)-1-hydroxyethyl)-1-methyl-2-oxo-1-carbapenam-3-carboxylate and 389 mg of cyclohepten-1-yl(tri-n-butyl)tin in the same manner as in Example 6.

IR(KBr)cm$^{-1}$: 1770, 1730,.1605, 1520, 1430, 1340.
NMR(CDCl$_3$) δ: 1.13(3H,d,J=8Hz), 1.36(3H,d,J=6Hz), 1.40–1.88(6H,m), 2.10–2.32(4H,m}, 3.20(1H,m), 3.29(1H,dd,J=3&7Hz), 4.16–4.42(2H,m), 5.22&5.46(2H,ABq,J=14Hz), 7.64(2H,d,J=9Hz), 8.24(2H,d,J=9Hz).

EXAMPLE 8

4-Nitrobenzyl (5R,6S)-2-(4-dimethylaminocarbonylphenyl)-6-((1R)-1-hydroxyethyl)-1-carbapen-2-em-3-carboxylate

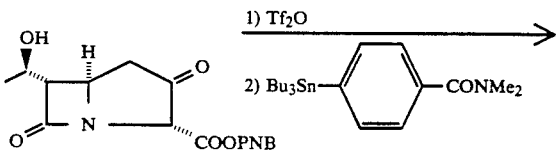

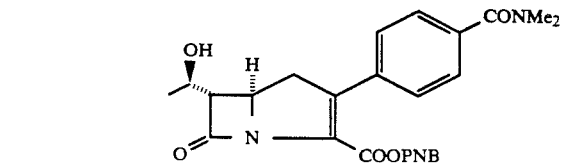

Under a nitrogen atmosphere, to a solution of 128 mg (0.368 mmol) of 4-nitrobenzyl (3R,5R,6S)-6-((1R)-1-hydroxyethyl) -2-oxo-1-carbapenam-3-carboxylate in acetonitrile (3 ml) was added 0.065 ml (0.37 mmol) of diisopropylethylamine followed by 0.062 ml (0.37 mmol) of trifluoromethanesulfonic anhydride at −45° C., and the mixture was stirred for 30 minutes. To the mixture was added ethyl acetate, and the organic layer was washed with saturated aqueous sodium bicarbonate followed by saturated aqueous sodium chloride. After the extract was dried over anhydrous magnesium sulfate, the solvent was removed. To the crude triflate was added 113 mg (0.83 mmol) of zinc chloride, 5.3 mg (0.0091 mmol) of bis(benzylideneacetone)palladium(0) and 4.4 mg (0.019 mmol) of tri(2-furyl)phosphine. Under a nitrogen atmosphere, to the mixture was added a solution of 191 mg (0.4436 mmol) of (4-dimethylaminocarbonylphenyl)tri-n-butyltin in N-methylpyrrolidinone (6 ml), and the mixture was stirred for 2 hours at room temperature. To the reaction mixture was added ethyl acetate, and the organic layer was washed with water (50 ml×2) followed by saturated aqueous sodium chloride. After the extract was dried over anhydrous magnesium sulfate, the solvent was removed. The residue was purified by silica gel column chromatography (elution with 3% methanol-chloroform) to give 9.1mg (yield: 27.9%) of the title compound.

IR(KBr)cm$^{-1}$: 1760, 1720, 1620, 1520, 1340, 1270, 1190.

NMR(CDCl$_3$) δ: 1.40(3H,d,J=6Hz), 3.00(3H,br-s), 3.13(3H,br-s), 3.10-3.30(3H,m), 4.20-4.40(2H,m), 5.22&5.41(2H,ABq,J=14Hz), 7.41(4H,s), 7.51(2H,d,J=9Hz), 8.21(2H,d,J=9Hz)

EXAMPLE 9

4-Nitrobenzyl (5R,6S)-2-(4-carbamoylphenyl)-6-((1R)-1-hydroxyethyl) -1-carbapen-2-em-3-carboxylate

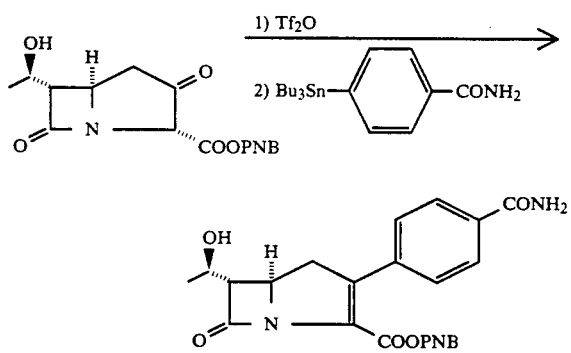

105 mg (yield: 46.5%) of the title compound was obtained from 174 mg of 4-nitrobenzyl (3R,5R,6S)-1-((1R)-1-hydroxyethyl)-2-oxo-1-carbapenam-3-carboxylate and 226 mg of (4-carbamoylphenyl)tri=n-butyltin in the same manner as in Example 8.

NMR(CDCl$_3$) δ: 1.4(3H,d,J=7Hz), 3.2-3.4(3H,m), 4.25(1H,m), 4.4(1H,dd,J=3&9Hz), 5.12&5.32(2H,ABq,J=14Hz), 6.0-6.3(2H,bd), 7.42(2H,d,J=8Hz), 7.46(2H,d,J=8Hz), 7.78(2H,d,J=8Hz), 8.18(2H,d,J=8Hz).

EXAMPLE 10

4-Nitrobenzyl (1S,5R,6S)-2-(4-carbamoylphenyl)-6-((1R)-1-hydroxyethyl) -1-methylcarbapen-2-em-3-carboxylate

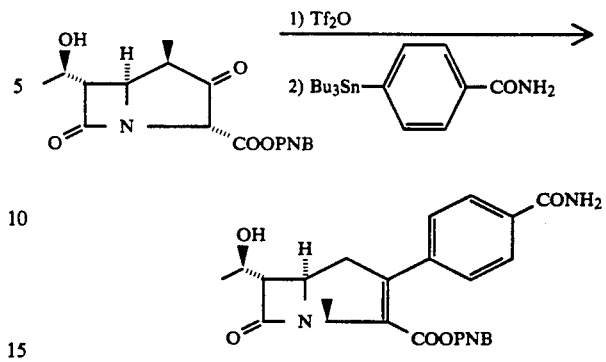

112 mg (yield: 30%) of the title compound was obtained from 295 mg of 4-nitrobenzyl (1R,3R,5R,6S)-6-((1R)-1-hydroxyethyl)-1-methyl-2-oxo-1-carbapenam-3-carboxylate and 399 mg of (4-carbamoylphenyl)tri-n-butyltin in the same manner as in Example 8.

NMR(DMSO-d$_6$) δ: 1.06(3H,d,J=6Hz), 1.34(3H,d,J=7Hz), 3.36-3.50(3H,m), 4.32(1H,m), 4.44(1H,dd,J=3&9Hz), 5.09&5.32(2H,ABq,J=15Hz), 6.3(1H,bs), 6.52(1H,bs), 7.38(4H,d,J=8Hz), 7.82(2H,d,J=8Hz), 8.03(2H,d,J=8Hz)

EXAMPLE 11

4-Nitrobenzyl (5R,6S)-2-(2-carbamoyl-4-thienyl)-6-((1R)-1-hydroxyethyl)-1-carbapen-2-em-3-carboxylate

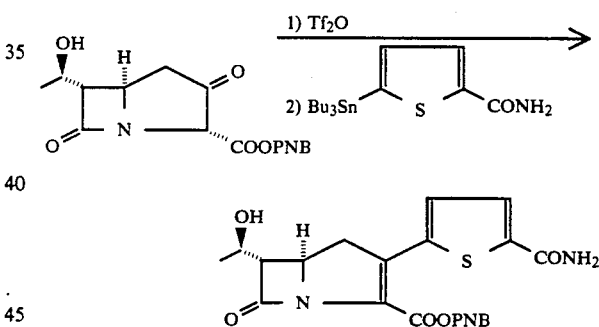

110 mg (yield: 34%) of the title compound was obtained from 250 mg of 4-nitrobenzyl (3R,5R,6S)-6-((1R)-hydroxyethyl) -2-oxo-1-carbapenam-3-carboxylate in the same manner as in Example 8.

NMR(DMSO-d6) δ: 1.2(3H,d,J=7Hz), 3.4(3H,m), 4.06(1H,dd,J=3&9Hz), 4.18(1H,m), 5.08(1H,dd,J=5Hz), 5.22&5.56(2H,ABq,J=16Hz), 7.5(1H,bs), 7.55(1H,d,J=4Hz), 7.72(1H,d,J=4Hz), 7.78(2H,d,J=9Hz), 8.09(1H,bs), 8.15(2H,d,J=9Hz)

EXAMPLE 12

4-Nitrobenzyl (5R,6S)-6-((1R)-1-hydroxyethyl)-2-methyl-1-carbapen -2-em-3-carboxylate

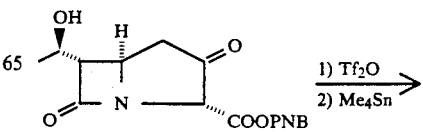

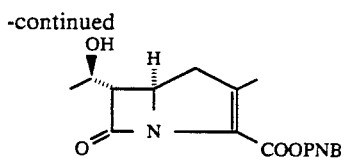

53.4 mg (yield: 41.9%) of the title compound was obtained from 128 mg of 4-nitrobenzyl (3R,5R,6S)-6-((1R)-1-hydroxyethyl) -2-oxo-1-carbapenam-3-carboxylate and 77.9 mg of tetramethyltin in the same manner as in Example 2 except that the coupling reaction time was changed to overnight.

IR(KBr)cm⁻¹: 1765, 1715, 1520, 1350, 1330.

NMR(CDCl₃) δ: 1.36(3H,d,J=6Hz), 2.17(3H,s), 2.89(2H,dd,J=1&10Hz), 3.16(1H,dd,J=3&7Hz), 4.10-4.40(2H,m), 5.25&5.50(2H,ABq,J=14Hz), 7.66(2H,d,J=9Hz), 8.24(2H,d,J=9Hz)

EXAMPLE 13

4-Nitrobenzyl (5R,6S)-6-((1R)-1-hydroxyethyl)-1-carbapen-2-em-3-carboxylate

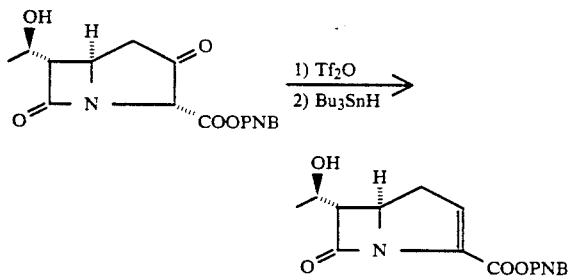

58.4 mg (yield: 23.9%) of the title compound was obtained from 256 mg of 4-nitrobenzyl (3R,5R,6S)-6-((1R)-1-hydroxyethyl)-2-oxo-1-carbapenam-3-carboxylate and 0.99 ml of tri-n-butyltin hydride in the same manner as in Example 2 except that the coupling reaction time was changed to overnight.

IR(KBr)cm⁻¹: 1780, 1730, 1610, 1520, 1350.

NMR(CDCl₃) δ: 1.36 (3H,d,J=6Hz), 2.70-3.20(2H,m), 3.25(1H,dd,J=3&7Hz), 4.10-4.40(2H,m), 5.30&5.48(2H,ABq,J=14Hz), 6.60(1H,m), 7.64(2H,d,J=9Hz), 8.26(2H,d,J=9Hz).

EXAMPLE 14

4-Nitrobenzyl (5R,6S)-2-benzyl-6-((1R)-1-hydroxyethyl)-1-carbapen-2-em-3-carboxylate

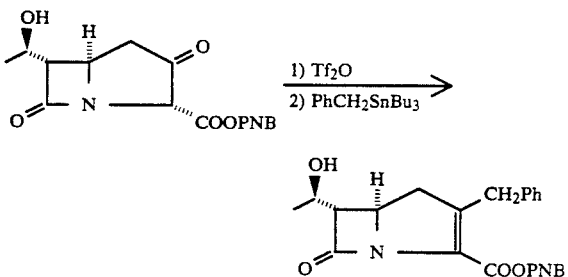

83.3 mg (yield: 53.6%) of the title compound obtained from 128 mg of 4-nitrobenzyl (3R,5R,6S)-6-((1R)-1-hydroxyethyl) -2-oxo-1-carbapenam-3-carboxylate and 166 mg of benzyl(tri-n-butyl)tin in the same manner as in Example 2 except that the coupling reaction time was changed to overnight.

IR(KBr)cm⁻¹: 1770, 1720, 1520, 1350, 1330, 1280.

NMR(CDCl₃) δ: 1.32(3H,d,J=6Hz), 2.78(2H,dd,J=5&9Hz), 3.12(1H,dd,J=3&7Hz), 3.92&4.05(2H,ABq,J=15Hz), 4.06-4.35(2H,m), 5.30&5.55(2H,ABq,J=15Hz), 7.10-7.40(5H,m), 7.68(2H,d,J=9Hz), 8.25(2H,d,J=9Hz).

EXAMPLE 15

4-Nitrobenzyl (5R,6S)-6-((1R)-1-hydroxyethyl)-2-methoxymethyl -1-carbapen-2-em-3-carboxylate

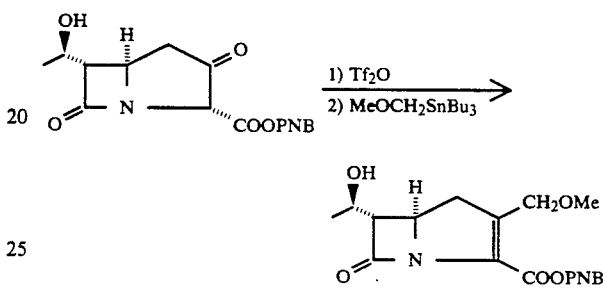

45.3 mg (yield: 32.7%) of the title compound was obtained from 4-nitrobenzyl (3R,5R,6S)-6-((1R)-1-hydroxyethyl) -2-oxo-1-carbapenam-3-carboxylate and 146 mg of methoxymethyl(tri-n-butyl)tin in the same manner as in Example 2 except that the coupling reaction time was changed to 3 days.

IR(KBr)cm⁻¹: 1770, 1610, 1520, 1450, 1350.

NMR(CDCl₃) δ: 1.34(3H,d,J=6Hz), 2.79-3.03(2H,m), 3.22(1H,dd,J=2&7Hz), 3.35(3H,s), 4.00-4.38(2H,m), 4.35&4.60(2H,ABq,J=14Hz), 5.26&5.50(2H,ABq,J=14Hz), 7.66(2H,d,J=9Hz), 8.24(2H,d,J=9Hz).

EXAMPLE 16

4-Niteobenzl (1S,5R,6S)-6-((1R)-1-hydroxyethyl)-2-(1-propynyl) -1-methylcarbapen-2-em-3-carboxylate

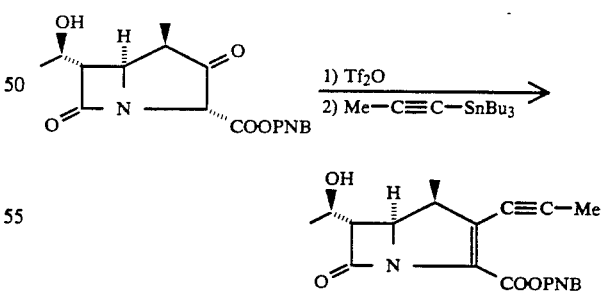

200 mg (yield: 48.7%) of the title compound was obtained from 387 mg of 4-nirobenzyl (1R,3R,5R,6S)-6-((1R) -1-hydroxyethyl)-2-oxo-1-methylcarbapen-2-em-3-carboxylate and 413 mg of (1-propynyl)tri-n-butyltin in the same manner as in Example 2.

NMR(CDCl₃) δ: 1.2(3H,d,J=6Hz), 1.3(3H,d,=6Hz), 2.97(3H,s), 3.08(1H,m), 3.34(1H,dd,J=3&9Hz), 5.2&5.4(2H,ABq,J=15Hz), 7.68(2H,d,J=8Hz), 8.22(2H,d,J=8Hz).

EXAMPLE 17

4-Ntrobenzyl (5R,6S)-2-(3,3-dimethyl-1-burtynyl)-6-((1R)-1-hydroxyethyl)-1-carbapen-2-em-3-caboxylate

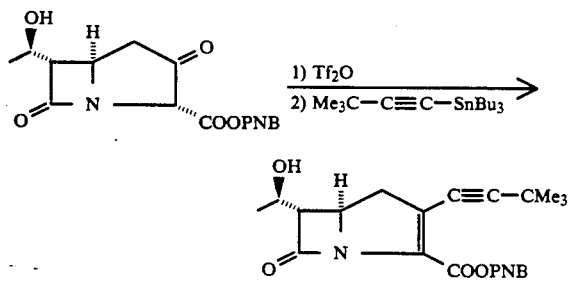

95.1 mg (31.4%) of the title compound was obtained from 256 mg of 4-nitrobenzyl (3R,5R,6S)-6-((1R)-1-hydroxyethyl)-2-oxo-1-carbapenam-3-carboxylate and 328 mg of (3,3-dimethyl-1-butynyl)tri-n-butyltin in the same manner as in Example 2.

NMR(CDCl$_3$) δ: 1.22(9H,s), 1.34(3H,d,J=7Hz), 2.4(2H,bs), 3.22(1H,dd,J=3&6Hz), 4.22(1H,dd,J=3&9Hz), 4.82(1H,bs), 5.3&5.5(2H,ABq,J=124Hz), 7.62(2H,d,J=8Hz), 8.2(2H,d,J=8Hz).

EXAMPLE 18

4-Nitrobenzyl (5R,6S)-2-N,N-dimethylcarbamoylethynyl-6-((1R)-1-hydroxyethyl)-1-carbapen-2-em-3-carboxylate

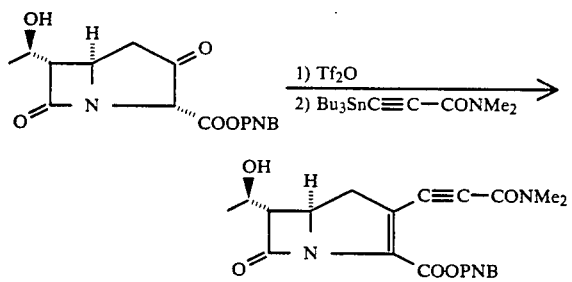

158 mg (yield: 46.1%) of the titel compound was obtained rom 348 mg of 4-nitrobenzyl 93R,5R,6S)-6-((1R)-1-hydroxyethyl)-2-oxo-1-carbapenam-3-carboxylate and 618 mg of N,N-dimethylcarbamoylethynyl (tri-n-butyl)tin in the same manner as in Example 2.

NMR(CDCl$_3$) δ: 1.38(3H,d,J=7Hz), 3.02(3H,s), 3.16(2H,t,J=9Hz), 3.04(3H,s), 3.38(1H,dd,J=3&6Hz), 4.28(1H,m), 4.4(1H,dd,J=3&9Hz), 5.32&5.54(2H,ABq,J=14Hz), 7.69(2H,d,J=8Hz), 8.28(2H,d,J=8Hz).

EXAMPLE 19

Sodium (5R,6S)-6-((1R)-1-hydroxyethyl)-2-vinyl-1-carbapen-2-em-3-carboxylate

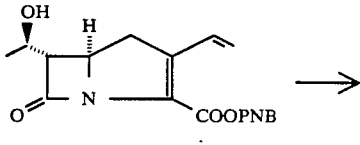

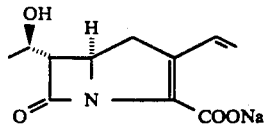

To a solution of 55.5 mg (0.0156 mmol) of the compound prepared in Example 2 in THF (7 ml) was added 1.9 ml of 1M aqueous ammonium chloride followed by 236 mg of iron powder under ice-cooling, and the mixture was stirred. After 20 minutes, to the mixture was added again 0.14 ml of 1M aqueous ammonium chloride and 236 mg of iron powder. The mixture was stirred for 40 minutes under ice-cooling, and then for 2 hours at room temperature. After an insoluble matter was removed by filtration, to the solution was added 5 ml of 0.1 M phosphate buffer (pH 7.0) and 30 ml of chloroform, and the aqueous layer was separated. The aqueous layer was washed again with 30 ml of chloroform, and purified by reverse phase silica gel column chromatography (elution with water). The desired fraction was collected and lyophilized to give 20.7 mg (yield: 54.2%) of the title compound.

UVλmax (0.1 M MOPS buffer, pH 7.0): 294 nm (ε=4,900)

IR(KBr)cm$^{-1}$: 1760, 1620, 1400.

NMR(D$_2$O) δ: 1.21(3H,d,J=6Hz), 2.97(2H,d,J=10Hz), 2.32(1H,dd,J=2&6Hz), 4.03–4.32(2H,m), 5.31(1H,d,J=12Hz), 5.46(1H,d,J=17Hz), 7.13(1H,dd,J=12&17Hz).

EXAMPLE 20

Sodium (1S,5R,6S)-6-((1R)-1-hydroxyethyl)-2-vinyl-1-methyl-carbapen-2-em-3-carboxylate

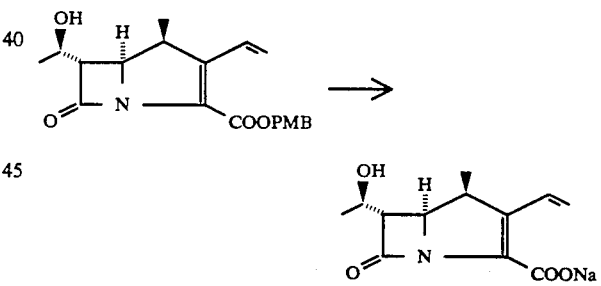

To the mixed solvent of 1.4 ml of anisole and 0.2 ml of dichlorome&hane was added 50.5 mg (0.38 mmol) of anhydrous aluminium chloride, and the mixture was cooled to −60° C. To this mixture was added a solution of 33.7 mg (0.0944 mmol) of the compound prepared in Example 5 in 1.4 ml of anisole and 0.2 ml of dichloromethane, and the mixture was stirred for 30 minutes at the same temperature. And then, to the mixture was added a solution of 143 mg (1.7 mmol) of sodium bicarbonate in 4 ml of 0.1 M phosphate buffer (pH 7.0), and the mixture was stirred for 30 minutes under ice-cooling. After the reaction mixture was filtered, the filtration was washed twice with dichloromethane. The aqueous layer was separated, and purified by reverse phase silica gel column chromatography (elution with 10% methanol-water) to give 5.74 mg (yield: 23.5% of the title compound.

UVλmax (0.1 M MOPS buffer, pH 7.0): 298 nm (ε=8,900)

IR(KBr)cm⁻¹: 1750, 1600, 1400.

NMR(D₂O) δ: 1.15(3H,d,J=6Hz), 1.29(3H,d,J=6Hz), 3.33-3.55(2H,m), 4.15(1H,dd,J=2&8Hz), 4.23(1H,m), 5.40(1H,d,J=11Hz), 5.55(1H,d,J=18Hz), 7.13(1H,dd,J=11&18Hz).

EXAMPLE 21

Sodium (1S,5R,6S)-6-((1R)-1-hydroxyethyl)-2-vinyl-1-methyl-carbapen-2-em-3-carboxylate

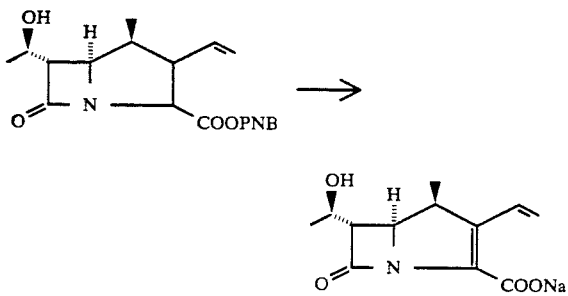

9.8 mg (yield: 3.4.4%) of the title compound was obtained from 41 mg o the compound prepared in Example 4 in the same manner as in Example 19. Physical data of this compound agreed with the data of the compound prepared in Example 20.

EXAMPLE 22

4-Nitrobenzyl (5R,6S)-6-((1R)-1-hydroxyethyl)-2-(1-methylvinyl)-1-carbapen-2-em-3-carboxylate

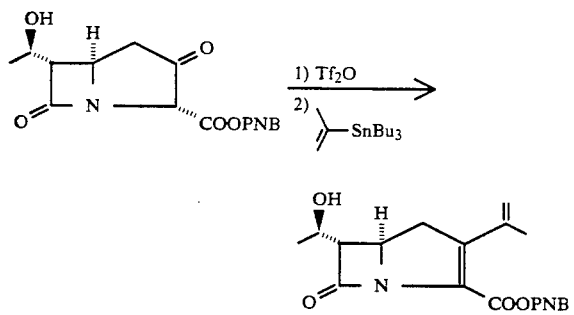

582 mg (yield: 42.5%) of the title compound was obtained from 1.28 g of 4-nitrobenzyl (3R,5R,6S)-6-((1R)-1-hydroxyethyl)-2-oxo-1-carbapenam-3-carboxylate and 1.44 g of 1-methylvinyl(tri-n-butyl)tin in the same manner as in Example 2 except that the couple reaction condition was changed to room temperature overnight followed by at 50° C. for 1 hour.

IR(KBr)cm⁻¹: 1780, 1730, 1520, 1340.

NMR(CDCl₃) δ: 1.35(3H,d,J=6Hz), 1.92(3H,s), 3.07(1H,d,J=10Hz), 3.10(1H,d,J=9Hz), 5.18(1H,s), 5.29&5.45(2H,ABq,J=13Hz), 7.65(2H,d,J=9Hz), 8.24(2H,d,J=9Hz).

EXAMPLE 23

Sodium (5R,6S)-6-((1R)-1-hydroxyethyl)-2-(1-methylvinyl)-1-carbapen-2-em-3-carboxylate

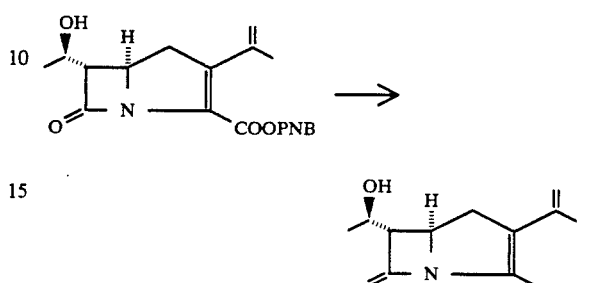

84.4 mg (yield: 27.9%) of the title compound was obtained from 436 mg of the compound prepared in Example 22 in the same manner as in Example 19.

UVλmax (0.1 M MOPS buffer, pH 7.0): 287 nm (ε=5,300)

IR(KBr)cm⁻¹: 1750, 1600, 1400, 1130, 1080.

NMR(D₂O) δ: 1.25(3H,d,J=6Hz), 1.90(3H,s), 2.95(1H,d,J=10Hz), 3.03(1H,d,J=8Hz), 3.41(1H,dd,J=3&6Hz), 4.08-4.25(2H,m), 4.96(1H,s), 5.02(1H,s),

EXAMPLE 24

4-Nitrobenzyl (1S,5R,6S)-1-((1R)-1-hydroxyethyl)-2-(1-methylvinyl)-1-methylcarbapen-2-em-3-carboxylate

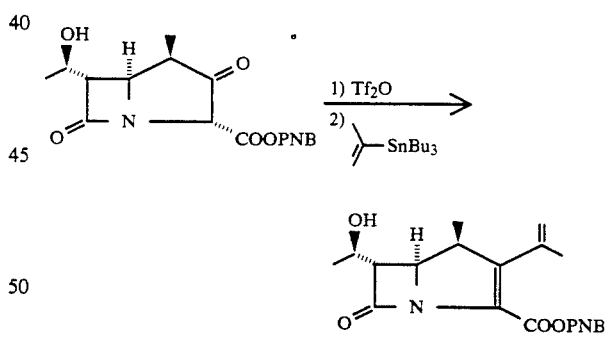

54.5 mg (yield: 38.5%) of the title compound was obtained from 133 mg of 4-nitrobenzyl (1R,3R,5R,6S)-6-((1R)-1-hydroxyethyl)-2-oxo-1-methylcarbapenam-3-carboxylate and 144 mg of 1-methylvinyl(tri-n-butyl)tin in the same manner as in Example 2 except that the coupling reaction condition was changed to room temperature overnight followed by at 50° C. for 1 hour.

IR(KBr)cm⁻¹: 1770, 1730, 1520, 1350.

NMR(CDCl₃) δ: 1.16(3H,d,J=7Hz), 1.36(3H,d,J=6Hz), 1.93(3H,s), 3.24(1H,dd,J=7&10 Hz), 3.32(1H,dd,J=3&7Hz), 4.20-4.39(2H,m), 5.02(1H,s), 5.23(1H,s), 5.26&5.46(2H,ABq,J=14Hz), 7.66(2H,d,J=9Hz), 8.25(2H,d,J=9Hz).

EXAMPLE 25

Sodium (1S,5R,6S)-6-((1R)-1-hydroxyethyl)-2-(1-methylvinyl)-1-methylcarbapen-2-em-3-carboxylate

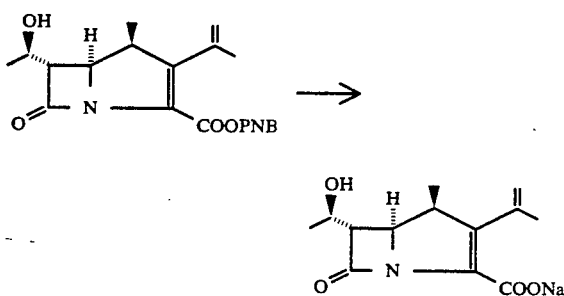

23.5 mg (44.8%) of the title compound was obtained from 74.2 mg of the compound prepared in Example 24 in the same manner as in Example 19.

UVλmax (0.1 M MOPS buffer, pH 7.0): 284 nm (ε=5,600).

IR(KBr)cm$^{-1}$: 1750, 1640, 1620, 1400.

NMR(D$_2$O) δ: 1.10(3H,d,J=7Hz), 1.27(3H,d,J=6Hz), 1.90(3H,s), 3.27(1H,m), 3.41(1H,dd,J=2&6Hz), 4.15(1H,dd,J=2&9Hz), 4.22(1H,m), 5.08(2H,s).

EXAMPLE 26

Pivaloyloxymethyl (1S,5R,6S)-6-((1R)-1-hydroxyethyl)-2-(1-methylvinyl)-1-methylcarbapen-2-em-3-carboxylate

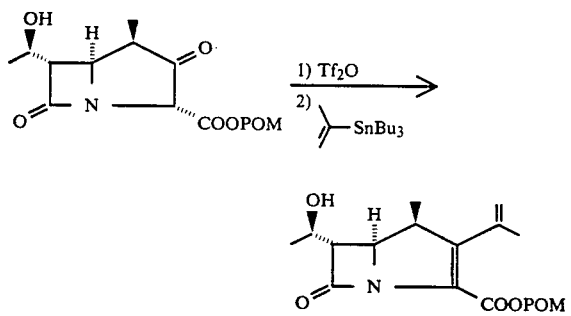

51.6 mg (yield: 32.4%) of the title compound was obtained from 152 mg of pivaloyloxymethyl (1S,5R,6S)-6-((1R) -1-hydroxyethyl)-2-oxo-1-methylcarbapenam-3-carboxylate and 171 mg of 1-methylvinyl(tri-n-butyl)tin in the same manner as in Example 2 except that the coupling reaction condition was changed to room temperature overnight followed by at 50° C. for 1 hour.

IR(KBr)cm$^{-1}$: 1780, 1760, 1280, 1200, 1120.

NMR(CDCl$_3$) δ: 1.15(3H,d,J=7Hz), 1.21(9H,s), 1.33(3H,d,J=6Hz), 1.91(3H,s), 3.22(1H,dd,J=7&10Hz), 3.29(1H,dd,J=3&7Hz), 4.10–4.32(2H,m), 4.99(1H,s), 5.19(1H,s), 5.84&5.91(2H,ABq,J=7Hz).

EXAMPLE 27

4-Nitrobenzyl (1S,5R,6S)-6-((1R)-1-hydroxyethyl)-2-(2-methyl-1-propenyl)-1-methylcarbapen-2-em-3-carboxylate

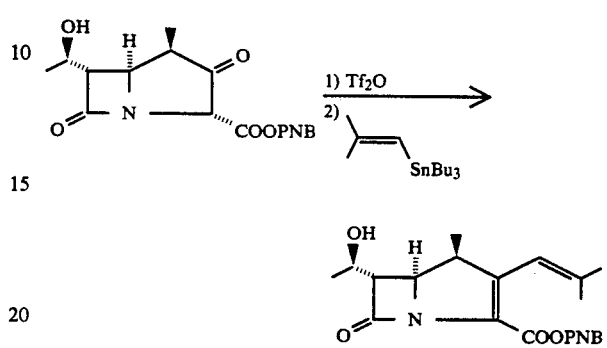

60.8 mg (yield: 41.4%) of the title compound was obtained form 133 mg of 4-nitrobenzyl (1R,3R,5R,6S)-6-((1R)-1-hydroxyethyl) -2-oxo-1-methylcarbapenam-3-carboxylate and 150 mg of 2-methyl-1-propenyl(tri-n-butyl)tin in the same manner as in Example 2 except that the coupling reaction time was changed to overnight.

IR(KBr)cm$^{-1}$: 1770, 1710, 1520, 1340.

NMR(CDCl$_3$) δ: 1.14(3H,d,J=7Hz), 1.37(3H,d,J=6Hz), 1.81(3H,s), 1.91(3H,s), 3.28(1H,dd,J=3&7Hz), 3.49(1H,m), 4.16–4.44(2H,m), 5.27&5.50(2H,ABq,J=14Hz), 6.50(1H,s), 7.69(2H,d,J=9Hz), 8.25(2H,d,J=9Hz).

EXAMPLE 28

Sodium (1S,5R,6S)-6((1R)-1-hydroxyethyl)-2-(2-metyl-1-propenyl) -1-methylcarbapen-2-em-3-carboxylate

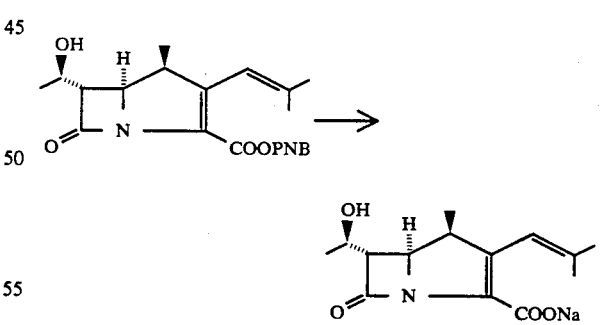

17.8 mg (yield: 41.1%) of the titel compound was obtained from 60.5 mg of the compound prepared in Example 27 in the same manner as in Example 19. UVλmax (0.1M MOPS buffer, pH 7.0): 297 nm(ε=6,000).

IR(KBr)cm$^{-1}$: 1750, 1620, 1400.

NMR(D$_2$O) δ: 1.05(3H,d,J=7Hz), 1.26(3H,d,J=6Hz), 1.69(3H,s), 1.81(3H,s), 3.22(1H,m), 3.34(1H,dd,J=2&6Hz), 4.12(1H,dd,J=2&10Hz), 4.21(1H,m), 6.06(1H,s).

Example 29

4-Nitrobenzyl (5R,6S)-6-((1R)-1-hydroxyethyl)-2-(1-propenyl) -1-carbapen-2-em-3-carboxylate

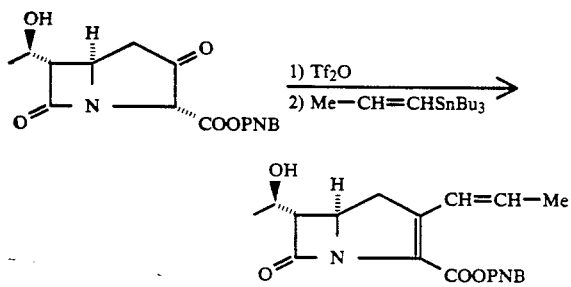

84.7 mg (yield: 61.9%) of the titel compound was obtained form 128 mg of 4-nitrobenzyl (3R,5R,6S)-6-((1R)-1-hydroxytehyl) -2-oxo-1-carbapenam-3-carboxylate and 144 mg of 1-propenyl(tri-n-butyl)tin (trans:cis =ca. 1:1) in the same manner as in Example 2.

IR(KBr)cm$^{-1}$: 1770, 1710, 1520, 1340, 1290.
NMR(CDCl$_3$) δ: 1.38&1.39(total 3H, both d,J=6Hz), 1.77(3×⅓H,d,J=4Hz), 1.92(3×⅔H,d,J=6Hz), 2.86–3.42(3H,m), 4.12–4.38(2H,m), 5.28&5.29(total 1H, both d,J=14Hz), 5.54&5.55(total 1H, both d,J=14hz), 5.78–6.16(1H,m), 6.60&6.71(total 2H, both d,J=9Hz), 7.00(1×⅓GH,d,J=13Hz), 7.20(1×⅔H,d,J=16Hz), 8.26(2H,d,J=9Hz).

EXAMPLE 30

Sodium (5R,6S)-6-((1R)-1-hydroxsyethyl)-2-(1-propenyl)-1-carbapen -2-em-3-carboxylate

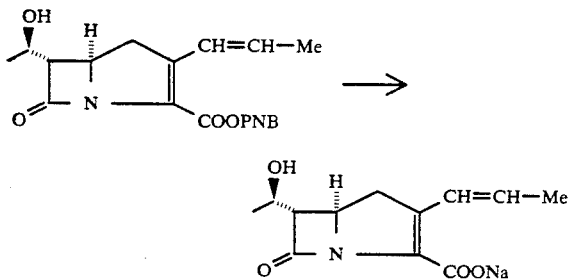

Deprotection reaction of 84.6 mg of the compound prepared in Example 29 was carried out in the same manner as in Example 19. 16.4 mg (yeild: 27.9%) of the E isomer of the title compound was obtained by the separation and purification using refers phase silica gel column chromatography. Because the separation was to sufficient, the pure Z isomer of the titel compound could not be isolated, but 3.7 mg of the E/Z mixture was obtained.

UVλmax (0.1M MOPS buffer, pH 7.0): 297 nm (ε=4,400).

IR(KBr)cm$^{-1}$: 1750, 1620, 1400.
NMR(D$_2$O) δ: 1.24(3H,d,J=7Hz), 1.80(3H,dd,J=1&7Hz), 3.00(2H,d,J=9Hz), 3.31(1H,dd,J=3&6Hz), 4.00–4.28(2H,m), 5.95(1H,m), 6.93(1H,d,J=16Hz).

EXAMPLE 31

4-Nitrobenzyl (1S,5R,6S)-6((1R)-1-hydroxtytehyl)-2-(1-propenyl) -1-methylcarbapen-2-em-3-carboxylate

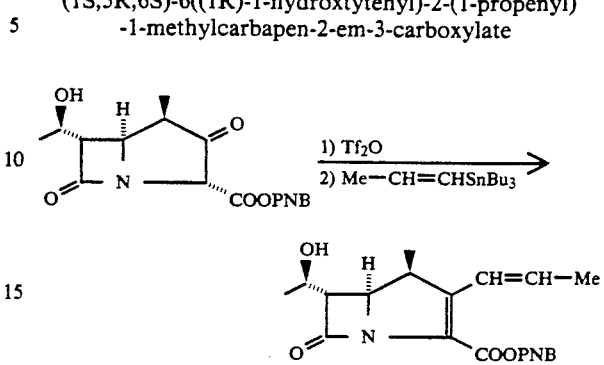

78.4 mg (yield: 55.3%) of the title compound was obtained from 133 mg of 4-nitrobenzyl (1R,3R,5R,6S)-6-((1R) -1-hydroxyethyl)-2-oxo-1-methylcarbapenam-3-carboxylate and 144 mg of 1-propenyl(tri-n-butyl)tin (trans:cis =ca.1:1) in the same manner as in Example 2 except that the coupling reaction time was changed to overnight.

IR(KBr)cm$^{-1}$: 1770, 1710, 1520, 1340, 1300, 1200.
NMR(CDCl$_3$) δ: 1.17(3H,d,J=7Hz), 1.37(3H,d,J=6Hz), 1.86(3×⅔H,dd,J=2&7Hz), 1.92(3×⅓H,dd,J=2&7Hz), 3.22–3.66(2H,m), 4.07–4.43(2H,m), 5.27(1H,d,J=14Hz), 5.50&5.52(total 1H, both d,J=14Hz), 7.14(1×⅓H,d,J=16Hz) 7.70&7.71(total 2H, both d,J=9Hz), 8.24(2H,d,J=9Hz).

EXAMPLE 32

Sodium (1S,5R,6S)-6-((1R)-1-hydroxyethyl)-2-(1-propenyl)-1-methylcarbapen-2-em-3-carboxylate

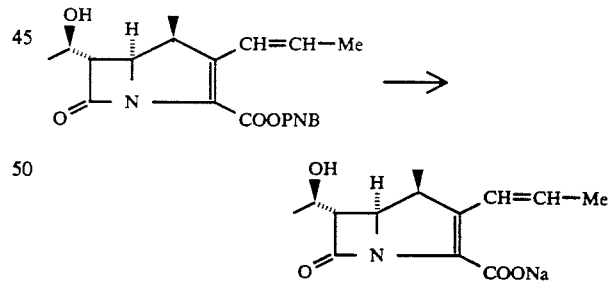

Deprotection reaction of 75.9 mg of the compound prepared in Example 31 was carried out in the same manner as in Example 19. 12.9 mg (yield: 24.0%) of the Z isomer of the title compound was obtained by the separation and purification using reverse phase silica gel column chromatography. Because the separation was not sufficient, the pure E form could not obtained, but 8.4 mg of the E/Z mixture was obtained.

UVλmax (0.1 M MOPS buffer, pH 7.0): 295 nm (ε=6,600)

IR(KBr)cm$^{-1}$: 1750, 1600, 1410.
NMR(D$_2$0) δ: 1.06(3H,d,J=7Hz), 1.25(3H,d,J=6Hz), 1.69(3H,dd,J=2&7Hz), 3.29(1H,m), 3.35(1H,dd,J=3&7Hz), 4.13(1H,dd,J=3&11Hz), 4.20(1H,m), 5.62-5.86(1H,m), 6.28(1H,dd,2&12Hz)

EXAMPLE 33

4-Nitrobenzyl (5R,6S)-2-((E)-2-carbamoylvinyl)-6-((1R)-1-hydroxyethyl) -1-carbapen-2-em-3-carboxylate

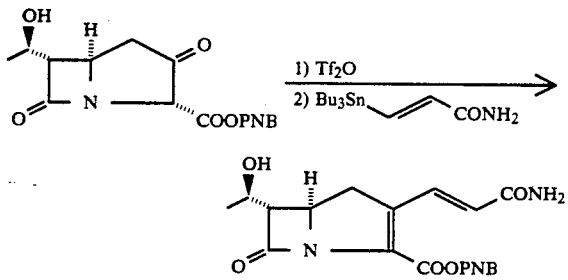

Under a nitrogen atmosphere, to a solution of 128 mg (0.367 mmol) of 4-nitrobenzyl (5R,6S)-2-oxo-6-((1R)-1-hydroxyethyl) -1-carbapenam-3-carboxylate in acetonitrile (3ml) was added 0.065 ml (0.37 mmol) of diisopropylethylamine at −45° C., followed by 0.062 ml (0.37 mmol) of trifluoromethanesulfonic anhydride, and the mixture was stirred at −40°-30° C. for 30 minutes. To the reaction mixture was added ethyl acetate (3 ml), and the organic layer was washed with saturated aqueous sodium bicarbonate followed by saturated aqueous sodium chloride. After the extract was dried over anhydrous magnesium sulfate, the solvent was removed. The residual triflate was used the next reaction without purification. To this crude product was added 113 mg (0.83 mmol) of zinc chloride, 5.3 mg (0.0091 mmol) of bis(-benzylideneacetone)palladium(0), and 4.4 mg (0.0185 mmol) of tri(2-furyl)phosphine. Under a nitrogen atmosphere, a solution of 157 mg (0.436 mmol) of (E)-2-carbamoylvinyl (tri-n-butyl)tin in N-methylpyrrolidinone (6 ml) was added, and the mixture was stirred for 2 hours at room temperature. To the reaction mixture was added ethyl acetate, and the organic layer was washed with water followed by saturated aqueous sodium chloride. After the extract was dried over anhydrous magnesium sulfate, the solvent was removed. The residue was purified by silica gel column chromatography (elution with methanol-chloroform system) to give 50.5 mg (yield: 34.3 %) of the title compound.

IR(KBr)cm$^{-1}$: 1780, 1720, 1650, 1600, 1520, 1340, 1270.

NMR(CDl$_3$-CD$_3$OD) δ: 1.35(3H,d,J=6Hz), 3.16(2H,dd,J=4&6Hz), 3.30(1H,dd,J=3&7Hz), 4.10-4.38(2H,m), 5.38&5.56(2H,ABq,J=13Hz), 6.21(1H,d,J=15Hz), 7.74(2H,d,J=8Hz), 8.21(1H,d,J=15Hz), 8.27(2H,d,J=8Hz).

EXAMPLE 34

Sodium (5R,6S)-2-((E)-2-carbamoylvinyl)-6-((1R)-1-hydroxyethyl) -1-carbapen-2-em-3-carboxylate

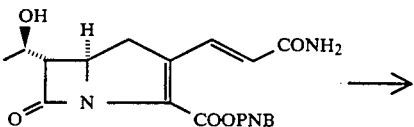

-continued

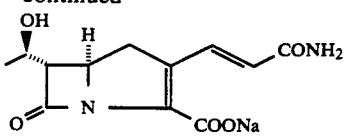

To a solution of 50.5 mg (0.126 mmol) of the compound prepared in Example 33 in THF (5.5 ml) was added 1.5 ml of 1M aqueous ammonium chloride followed by iron 191 mg of iron powder under ice-cooling, and the mixture was stirred for 20 minutes at the same temperature and then for 20 minutes at room temperature. The operation, addition of 191 mg of iron powder and then stirring for 20 minutes at room temperature, was repeated three times. After an insoluble matter was removed by filtration, to the solution was added 9 ml of 0.1 M phosphate buffer (pH 7.0) and chloroform, and the aqueous layer was separated. The aqueous layer was washed with chloroform, and purified by reverse phase silica gel column chromatography (elution with water). The desired fraction was collected and lyophilized to give 21.5 mg (yield: 59.2%) of the title compound.

UVλmax (0.1 M MOPS buffer, pH 7.0): 322 nm (ε=6,900).

IR(KBr)cm$^{-1}$: 1760, 1670, 1610, 1400.

NMR(D$_2$O) δ: 1.24(3H,d,J=6Hz), 3.08(2H,d,J=9Hz), 3.48(1H,dd,J=3&6Hz). 4.12-4.39(2H,m), 6.06(1H,d,J=16Hz), 7.94(1H,d,J=16Hz)

EXAMPLE 35

4-Nitrobenzyl (1S,5R,6S)-2-((E)-2-carbamoylvinyl)-6-((1R) -1-hydroxyethyl)-1-methylcarbapen-2-em-3-carboxylate

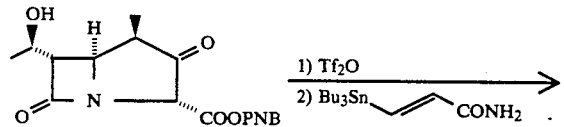

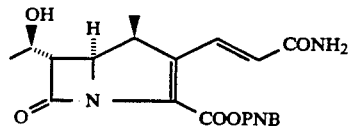

90.2 mg (yield: 59.2%) of the title compound was obtained from 133 mg of 4-nitrobenzyl (1R,3R,5R,6S)-6-((1R) -1-hydroxyethyl)-2-oxo-1-methylcarbapenam-3carboxylate in the same manner as in Example 33 except that the coupling reaction time was changed to 6 hour.

IR(KBr)cm$^{-1}$: 1770, 1720, 1670, 1600, 1520, 1340, 1290.

NMR(CDCl$_3$+CD$_3$OD) δ: 1.24(3H,d,J=8Hz), 1.34(3H,d,J=6Hz), 3.27-3.50(2H,m), 4.10-4.34(2H,m), 5.34&5.52(2H,ABq,J=14Hz), 6.22(1H,d,J=16Hz), 7.70(2H,d,J=9Hz), 8.10(1H,d,J=16Hz), 8.26(2H,d,J=9Hz).

EXAMPLE 36

Sodium (1S,5R,6S)-2-((E)-2-carbamoylvinyl)-6-((1R)-1-hydroxyethyl)-1-methylcarbapen-2-em-3-carboxylate

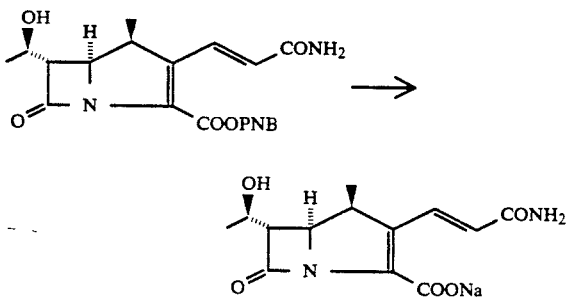

26.2 mg (yield: 40.7%) of the title compound was obtained from 88.5 mg of the compound prepared in Example 35 and 1.288 g (322 mg×4) of iron powder in the same manner as in Example 34.

UVλmax (0.1 M MOPS buffer, pH 7.0): 327 nm (ε=15,400)

IR(KBr)cm$^{-1}$: 1750, 1660, 1600, 1380, 1260.

NMR(D$_2$O) δ: 1.12(3H,d,J=7Hz), 1.24(3H,d,J=6Hz), 3.26–3.52(2H,m), 4.10–4.30(2H,m), 6.19(1H,d,J=16Hz), 7.82(1H,d,J=16Hz).

EXAMPLE 37

4-Nitrobenzyl (5R,6S)-2-((E)-2-dimethylcarbamoylvinyl)-6-((1R)-1-hydroxyethyl)-1-carbapen-2-em-3-carboxylate

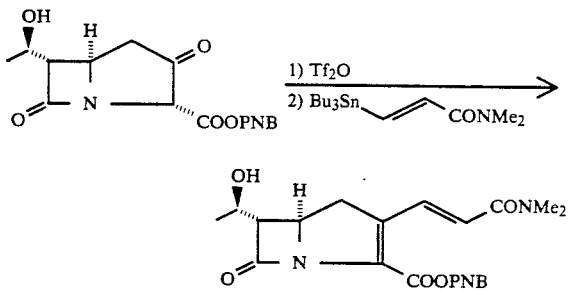

69.1 mg (yield: 43.9%) of the title compound was obtained from 128 mg of 4-nitrobenzyl (3R,5R,6S)-6-((1R)-hydroxyethyl)-2-oxo-1-carbapenam-3-carboxylate and 143 mg of (E)-2-dimethylcarbamoylvinyl(tri-n-butyl)tin in the same manner as in Example 33 except that the coupling reaction time was changed to overnight.

IR(KBr)cm$^{-1}$: 1780, 1720, 1640, 1600, 1520, 1350, 1290.

NMR(CDCl$_3$) δ: 1.34(3H,d,J=6Hz), 3.03(3H,s), 3.09(3H,s), 3.13(2H,m), 3.27(1H,dd,J=3&7Hz), 4.14–4.38(2H,m), 5.29&5.50(2H,ABq,J=14Hz), 6.41(1H,d,J=15Hz), 7:67(2H,d,J=9Hz), 8.16(1H,d,J=15Hz), 8.23(2H,d,J=9Hz).

EXAMPLE 38

Sodium (5R,6S)-2-((E)-2-dimethylcarbamoylvinyl)-6-((1R)-1-1-carbapen-2-em-3-carboxylate

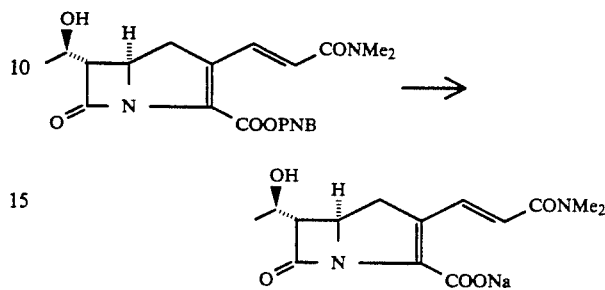

19.1 mg (yield: 38%) of the title compound was obtained from 68.1 mg of the compound prepared in Example and 964 mg (241 mg×4) of iron powder in the same manner as in Example 34.

UVλmax (0.1M MOPS buffer, pH 7.0): 324 nm (ε=15,200)

IR(KBr)cm$^{-1}$: 1760, 1640, 1600, 1390, 1250.

NMR(D20) δ: 1.28(3H,d,J=6Hz}, 3.00(3H,s), 3.10(2H,d,J=9Hz), 3.15(3H,s), 3.47(1H,dd,J=3&6Hz), 4.15–4.35(2H,m), 6.44(1H,d,J=16Hz), 7.90(1H,d,J=16Hz).

EXAMPLE 39

4-Nitrobenzyl (1S,5R,6S)-2-((E)-2-dimethyl-carbamoylvinyl)-6-((1R)-1-hydroxyethyl)-1-methylcarbapen-em-3-carboxylate

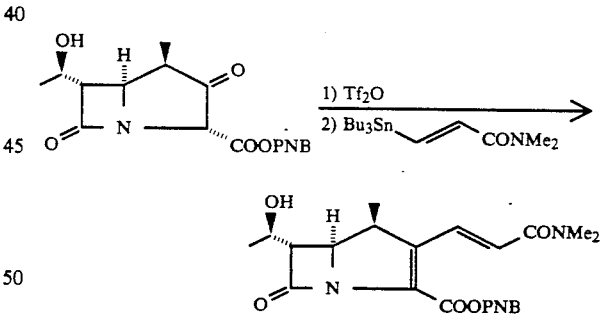

93.8 mg (yield: 57.7%) of the title compound was obtained from 165 mg of 4-nitrobenzyl (1R,3R,5R,6S)-6-((1R)-1-hydroxyethyl)-2-oxo-1-methylcarbapenam-3-carboxylate and 165 mg of (E)-2-dimethylaminocarbonylvinyl (tri-n-butyl)tin in the same manner as in Example 33 except that the coupling reaction time was changed to overnight.

IR(KBr)cm$^{-1}$: 1780, 1720, 1640, 1600, 1520, 1340, 1290.

NMR(CD$_2$C1$_3$) δ: 1.26(3H,d,J=7Hz), 1.36(3H,d,J=6Hz), 3.06(3H,s), 3.13(3H,s), 3.34(1H,dd,J=3&7Hz), 5.28&5.51(2H,ABq,J=14Hz), 6.62(1H,d,J=16Hz), 7.69(2H,d,J=9Hz), 8.15(1H,d,J=16Hz), 8.23(2H,d,J=9Hz).

EXAMPLE 40

Sodium (1S,5R,6S)-2-((E)-2-dimethylcarbamoylvinyl)-6-((1R)-1-hydroxyethyl)-1-methylcarbapen-2-em-3-carboxylate

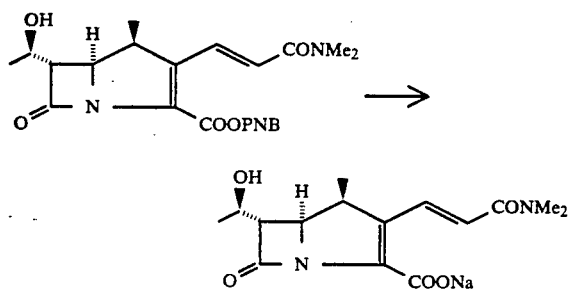

25.9 mg (yield: 37.4%) of the title compound was obtained from 93 mg of the compound prepared in Example 39 and 1.288 g (322 mg×4) of iron powder in the same manner as in Example 34.

UVλmax (0.1 M MOPS buffer, pH 7.0): 328 nm (ε=15,300).

IR(KBr)cm$^{-1}$: 1750, 1630, 1600, 1390, 1260.

NMR(D$_2$O) δ: 1.16(3H,d,J=8Hz), 1.27(3H,d,J=6Hz), 3.00(3H,s), 3.16(3H,s), 3.34–3.58(2H,m), 4.14–4.30(2H,m), 6.62(1H,d,J=16Hz), 7.84(1H,d,J=16Hz).

EXAMPLE 41

4-Nitrobenzyl (1S,5R,6S)-2-((Z)-2-carbamoylvinyl)-6-((1R)-1-hydroxyethyl)-1-methylcarbapen-2-em-3-carboxylate

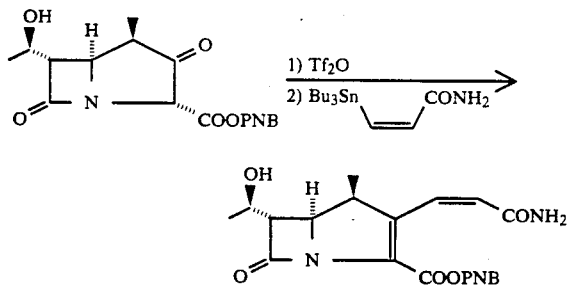

21.1 mg (yield: 13.9%) of the title compound was obtained from 133 mg of 4-nitrobenzyl (1R,3R,5R,6S)-6-((1R)-1-hydroxyethyl)-2-oxo-1-methylcarbapenam-3-carboxylate and 157 mg of (Z)-2-carbamoylvinyl(tri-n-butyl)tin in the same manner as in Example 33 except that the coupling reaction condition was changed to overnight at room temperature and then for 1 hour at 50° C.

IR(KBr)cm$^{-1}$: 1770, 1720, 1670, 1620, 1520, 1350.

NMR(CDCl$_3$) δ: 1.10(3H,d,J=8Hz), 1.33(3H,d,J=6Hz), 3.30(1H,dd,J=3&7Hz), 3.90(1H,m), 4.26(1H,m), 4.33(1H,dd,J=3&9Hz), 5.24&5.46(2H,ABq,J=13Hz), 5.88(1H,brs), 5.96(1H,brs), 6.05(1H,d,J=13Hz), 7.12(1H,d,J=13Hz), 7.66(2H,d,J=9Hz), 8.24(2H,d,J=9Hz).

EXAMPLE 42

Sodium (1S,5R,6S)-2-((Z)-2-carbamoylvinyl)-6-((1R)-1-hydroxyethyl)-1-methylcarbapen-2-em-3-carboxylate

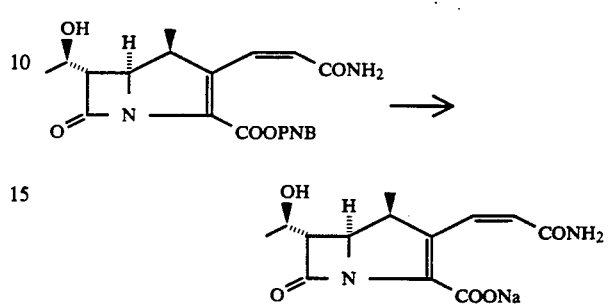

6.82 mg (yield: 46.9%) of the title compound was obtained from 20 mg of the compound prepared in Example 41 and 292 mg (73 mg×4) of iron powder in the same manner as in Example 34.

UVλmax (0.1 M MOPS buffer, pH 7.0): 315 nm (ε=3,500)

IR(KBr)cm$^{-1}$: 1750, 1640, 1620.

NMR(D$_2$O) δ: 1.03(3H,d,J=6Hz), 1.27(3H,d,J=6Hz), 3.36–3.70(2H,m), 4.10–4.42(2H,m), 6.04(1H,d,J=13Hz), 6.96(1H,d,J=13Hz).

EXAMPLE 43

4-Nitrobenzyl (5R,6S)-2-((Z)-2-dimethylcarbamoylvinyl)-6-((1R)-1-hydroxyethyl)-1-carbapen-2-em-3-carboxylate

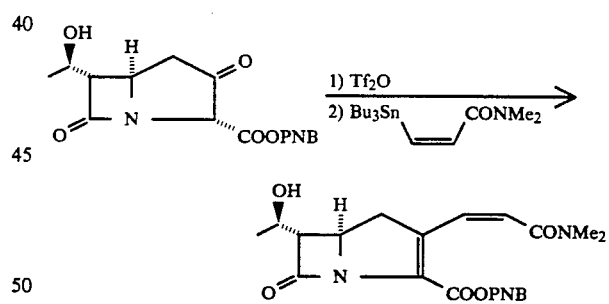

30 mg (yield: 16%) of the title compound was obtained from 128 mg of 4-nitrobenzyl (3R,5R,6S)-6-((1R)-1-hydroxyethyl)-2-oxo-1-carbapenam-3-carboxylate and 169 mg of (Z)-2-dimethylcarbamoylvinyl(tri-n-butyl)tin in the same manner as in Example 33 except that the coupling reaction time was changed to 24 hours.

IR(KBr)cm$^{-1}$: 1780, 1720, 1620, 1520, 1340, 1290.

NMR(CDCl$_3$) δ: 1.34(3H,d,J=6Hz), 3.01(3H,s), 3.04(3H,s), 3.10(2H,d,J=10Hz), 3.24(1H,dd,J=3&7Hz), 4.12–4.34(2H,m), 5.26&5.50(2H,ABq,J=14Hz), 6.21(1H,d,J=12Hz), 7.36(1H,d,J=12Hz), 7.68(2H,d,J=9Hz), 8.25(2H,d,J=9Hz).

EXAMPLE 44

Sodium (5R,6S)-2-((Z)-2-dimethylcarbamoylvinyl)-6-((1R)-1-hydroxyethyl)-1-carbapen-2-em-3-carboxylate

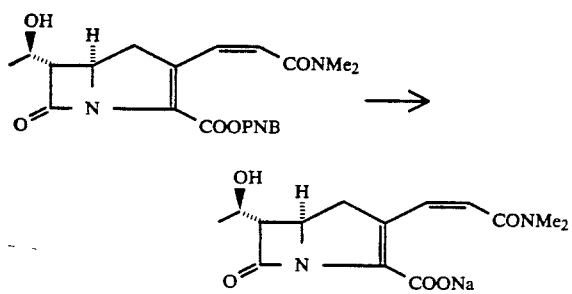

10.3 mg (yield: 48.4%) of the title compound was obtained from 28.9 mg of the compound prepared in Example 43 and 408 mg (102 mg×4) of iron powder in the same manner as in Example 34.

UVλmax (0.1 M MOPS buffer, pH 7.0): 306 nm ($\epsilon$ = 5,800)

NMR(D2O) δ: 1.26(3H,d,J=6Hz), 2.89(2H,d,J=10Hz), 2.97(3H,s), 3.07(3H,s), 3.42(1H,dd,J=3&6Hz), 4.09–4.29(2H,m), 6.10(1H,d,J=13Hz), 7.09(1H,d,J=13Hz).

EXAMPLE 45

4-Nitrobenzyl (1S,5R,6S)-2-((Z)-2-dimethylcarbamoylvinyl)-6-((.1R)-1-hydroxyethyl)-1-methylcarbapen-2-em-3-carboxylate

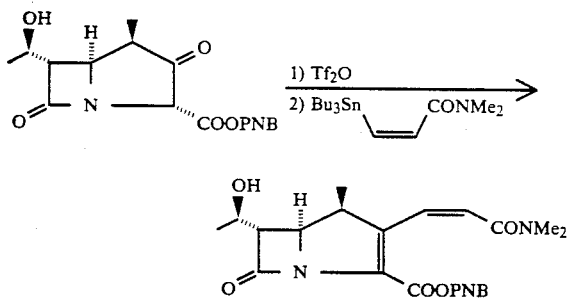

14.7 mg of (yield: 9%) of the title compound was obtained from 133 mg of 4-nitrobenzyl (1R,3R,5R,6S)-6-((1R)-1-hydroxyethyl)-2-oxo-1-methylcarbapenam-3carboxylate and 169 mg of (Z)-2-dimethylcarbamoylvinyl (tri-n-butyl)tin in the same manner as in Example 33 except that the coupling reaction condition was changed to overnight at room temperature and then for 3 hours at 50° C.

IR(KBr)cm$^{-1}$: 1780, 1720, 1640, 1620, 1260.

NMR(CDCl3) δ: 1.05(3H,d,J=8HZ), 1.35(3H,d,J=6Hz), 3.02(3H,s), 3.05(3H,s), 3.27(1H,dd,J=3&6Hz), 3.70(1H,m), 4.16–4.34(2H,m), 5.27&5.50(2H,ABq,J=14Hz), 6.23(1H,d,J=13Hz), 7.28(1H,d,J=13Hz), 7 68(2H,d,J=9Hz), 8.24(2H,d,J=9Hz).

EXAMPLE 46

Sodium (1S,5R,6S)-2-((Z)-2-dimethylcarbamoylvinyl)-6-((1R)-1-hydroxyethyl)-1-methylcarbapen-2-em-3-carboxylate

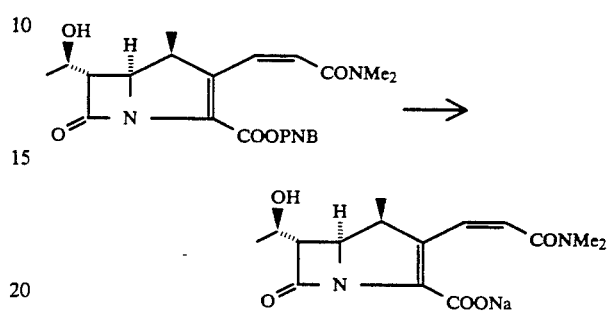

13.6 mg of the title compound was obtained from 14.7 mg of the title compound and 200 mg of iron powder (50 mg ×4) in the same manner as in Example 34.

UVλmax (0.1 M MOPS buffer, pH 7.0): 308 nm ($\epsilon$ = 3,000)

IR(KBr)cm$^{-1}$: 1750, 1620, 1450, 1400.

NMR(D2O) δ: 0.98(3H,d,J=8Hz), 1.26(3H,d,J=6Hz), 2.97(3H,s), 3.08(3H,S), 3.06–3.46(2H,m), 4.10–4.30(2H,m), 6.14(1H,d,J=13Hz), 7.03(1H,d,J=13Hz).

EXAMPLE 47

4-Nitrobenzyl (5R,6S)-2-(1-ethoxyvinyl)-6-((1R)-1-hydroxyethyl)-1-carbapen-2-em-3-carboxylate

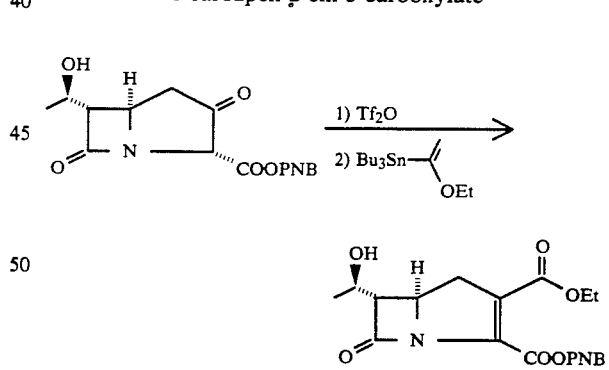

92.3 mg (yield: 62.6%) of the title compound was obtained from 128 mg of 4-nitrobenzyl (3R,5R,6S)-6-((1R)-hydroxyethyl)-2-oxo-1-carbapenam-3-carboxylate and 157 mg of 1-ethoxyvinyl(tri-n-butyl)tin in the same manner as in Example 33 except that the coupling reaction time was changed to overnight.

NMR(CDCl3) δ: 1.21(3H,t,J=6Hz), 1.33(3H,d,J=6Hz), 3.06(2H,d,J=9Hz), 3.30(1H,dd,J=3&6Hz), 3.75(2H,d,J=6Hz), 4.13–4.40(4H,m), 5.32&5.43(2H,ABq,J=14Hz), 7.63(2H,d,J=9Hz), 8.24(2H,d,J=9Hz).

EXAMPLE 48

Sodium
(5R,6S)-2-(1-ethoxyvinyl)-6-((1R)-1-hydroxyethyl)-1-carbapen-2-em-3-carboxylate

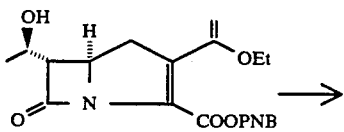

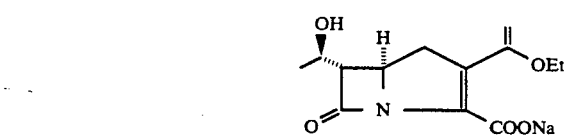

8.6 mg (yield: 13.0%) of the title compound was obtained from 92.3 mg of the compound prepared in Example 47 in the same manner as in Example 34.

UVλmax (0.1M MOPS buffer, pH 7.0): 322 nm.
IR(KBr)cm$^{-1}$: 1770, 1610, 1400.

EXAMPLE 49

4-Nitrobenzyl
(5R,6S)-2-((E)-2-carbamoyl-1-methylvinyl)-6-((1R)-1-hydroxyethyl)-1-carbapen-2-em-3-carboxylate

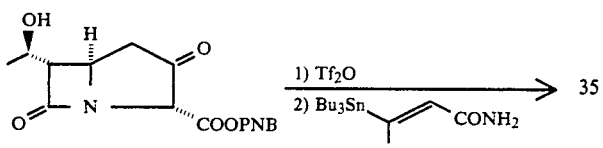

21.7 mg (yield: 14.2%) of the title compound was obtained rom 128 mg of 4-nirobenzyl (3R,5 R,6S)-6-((1R)-1-hydroxyethyl)-2-oxo-1-carbapenam-3-arboxylate in the same manner as in Example 33 except that the coupling reaction time was changed to overnight.

IR(KBr)cm$^{-1}$: 1780, 1730, 1670, 1610, 1520, 1350.
MRE(CDCl$_3$+CD$_3$OD) δ: 1.33(3H,d,J=6Hz), 2.25(3H,s), 3.03–3.34(3H,m), 4.10–4.36(2H,m), 5.29&5.42(2H,ABq,J=14Hz), 5.82(1H,s), 7.63(2H,d,J=9Hz), 8.25(2H,d,J=9Hz).

EXAMPLE 50

Sodium
(5R,6S)-2-((E)-2-carbamoyl-1-methylvinyl)-6-((1R)-1 -hydroxyetyl)-1-carbapen-2-em-3-carboxylate

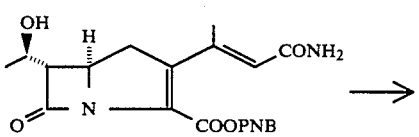

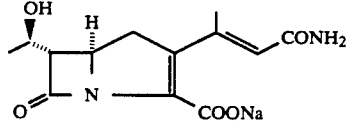

19.8 mg (yield: 78%) o he titel compound was obtained form 34.9 mg of the compound prepared in Example 49 in the same manner as in Example 34.

UVλmax (0.1M MOPS buffer, pH 7.0): 299 nm (ε=8,500).
IR(KBr)cm$^{-1}$: 1760, 1660, 1600, 1400.
NMR(D$_2$O) δ: 1.26(3H,d,J=6Hz), 2.13(3H,s), 2.84–3.27(2H,m), 3.44(1H,dd,J=3&6Hz), 4.11–4.31(2H,m), 5.84(1H,s).

EXAMPLE 51

4-Nitrobenzyl
(5R,6S)-2-(1-carbamoylvinyl)-6-((1R)-1-hydroxyethyl)-1-carbapen-2-em-3-carboxylate

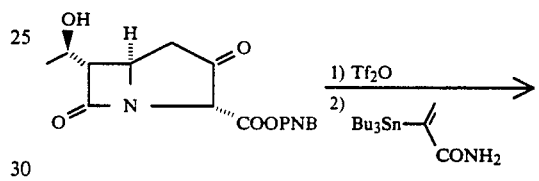

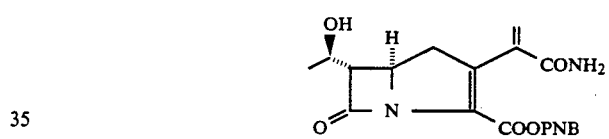

30.0 mg (yield: 20.6%) of the title compound was obtained form 128 mg of 4-nitrobenzyl (3R, 5R, 6S)-6-((1R)-1-hydroxyethyl)-2-oxo-1-carbapenam-3-carboxylate in the same manner as in Example 33 except that the coupling reaction time was changed to overnight.

IR(KBr)cm$^{-1}$: 1780, 1730, 1670, 1610, 1520, 1350.
NMR(CDCl$_3$+CD$_3$OD) δ: 1.32(3H,d,J=7Hz), 3.16(2H,m), 3.30(1H,dd,J=3&6Hz), 4.10–4.40(2H,m), 5.28&5.39(2H,ABq,J=13Hz), 5.60(1H,s), 6.05(1H,s), 7.62(2H,d,J=9Hz), 8.22(2H,d,J=9Hz).

EXAMPLE 52

Sodium
(5R,6S)-2-(1-carbamoylvinyl)-6((1R)-1-hydroxyethyl)-1-carbapen-2-em-3-carboxylate

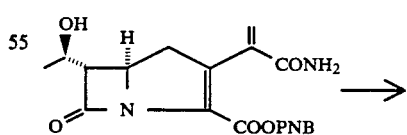

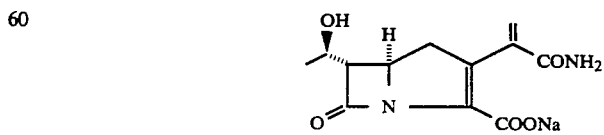

10.7 mg (yield: 49.3%) of the title compound was obtained from 30.2 mg o the compound prepared n Example 51 in he same manner as in Example 34.

UVλmax (0.1M MOPS buffer, pH 7.0): 296 nm (ε=2,300).

IR(KBr)cm$^{-1}$: 1760, 1670, 1610, 1410.

BMR(D$_2$O) δ: 1.27(3H,d,J=6Hz), 2.85–3.54(3H,m), 4.16–4.40(2H,m), 5.57(1H,s), 5.88(1H,s).

We claim:

1. A process for producing a 2-(unsubstituted or carbon substituted)-1-carbapen-2-em-3-carboxylic acid compound of the formula:

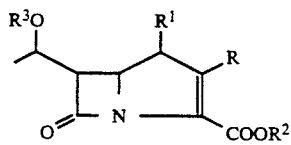
(I)

wherein R is a hydrogen atom or a substituent selected from the group consisting of lower alkyl, lower alkenyl, lower alkynyl, aryl, cycloalkenyl or non-fused or fused 5-membered or 6-membered heterocyclic group having art least one nitrogen, oxygen or sulfur atom, R$^1$ is a hydrogen atom or a methyl group, R$^2$ is a hydrogen atom or a carboxyl-protecting group, and R$^3$ is a hydrogen atom or a hydroxyl-protecting group, which comprises:

coupling a compound of the formula:

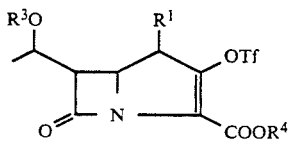
(III)

wherein R$^1$ and R$^3$ are as defined above, R$^4$ is a carboxyl-protecting group, and Tf is a triflorome-thanesulfonyl to a compound of the formula:

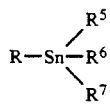
(II)

wherein R is as defined above, and each of R$^5$, R$^6$ and R$^7$, which may e the same or different, is a lower alkyl group, in an inert solvent in the presence of a palladium compound and a salt; and, optionally, removing any protecting group.

2. A process for producing a 2-(unsubstituted or carbon substituted)-1-carbapen-2-em-3-carboxylic acid compound of the formula:

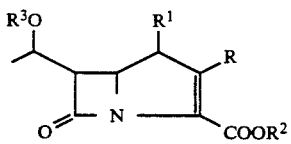
(I)

wherein R is a hydrogen atom or a substituent selected from the group consisting of lower alkyl, lower alkenyl, lower alkynyl, aryl, cycloalkenyl or non-fused or fused 5-membered or 6-membered heterocyclic group having at least one nitrogen, oxygen or sulfur atom, R$^1$ is a hydrogen atom or a methyl group, R$^2$ is a hydrogen atom or a carboxyl-protecting group, and R$^3$ is a hydrogen atom or a hydroxyl-protecting group, which comprises:

coupling a compound of the formula:

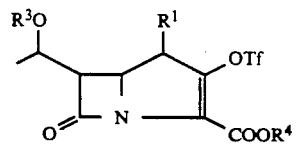
(III)

wherein R$^1$ and R$^3$ are as defined above, R$^4$ is a carboxyl-protecting group, and Tf is a triflorome-thanesulfonyl group, derived from a compound of the formula:

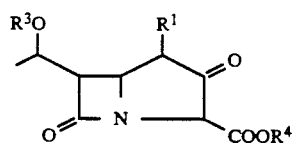
(IV)

wherein R$^1$, R$^3$ and R$^4$ are as defined above and trifluoromethanesulfonic anhydride, to a compound of he formula:

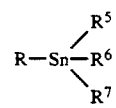
(II)

wherein R is as defined above, and each of R$^5$, R$^6$ and R$^7$, which may be the same or different, is a lower alkyl group, in an inert solvent n he presence of a palladium compound and a salt; and, optionally, removing any protecting group.

3. The process according o claim 1 or 2, wherein said palladium compound is tetrakis(triphenylphosphine)-palladium(O), bis(dibenzylideneacetone)palladium(O), tris(dibenzylideneacetone)dipalladium(O), dichlorobis(-triphenylphosphine)palladium(II), dichlorobis(benzonitrile)palladium(II), carbonyltris(triphenylphosphine)-palladium(O), trans-dimethylbis (triphenylphosphine)-palladium(II) or trans-(4-tert-butylcyclohexen-1-yl) chlorobis(triphenylphosphine)palladium(II).

4. The process according to claim 1 or 2, wherein said salt is a lithium halide, a sodium halide, a potassium halide, a zinc halide, a cesium halide or a quaternary ammonium halide.

5. The process according to claim 1 or 2, wherein said lower alkyl is methyl, ethyl, n-propyl, isopropyl, n-butyl, isobutyl, sec-butyl, t-butyl, n-pentyl, n-hexyl, isohexyl, cyclopropyl or cyclobutyl.

6. The process according to claim 1 or 2, wherein said lower alkenyl is binyl, 1-propenyl, 1-butenyl, 1-pentenyl or 1-hexenyl.

7. The process according to claim 1 or 2, wherein said lower alkynyl is ehtynyl, 1-propynyl, 1-butynyl, 1-pentynyl or 1-hexynyl.

8. The process according to claim 1 or 2, wherein said aryl is phenyl or a condensed polycyclic hydrocarbon.

9. The process according to claim 1 or 2, wherein said cycloalkenyl is cycloheptenyl.

10. The process according to claim 1 or 2, wherein said non-fused or fused heterocyclic group is pyrrolyl, imidazolyl, triazolyl, tetrazolyl, pyrazolyl, pyrrolidinyl, imidazolidinyl, pyrazolidinyl, pyrimidinyl, pyridyl, pyridinio, piperidyl, indolyl, thienyl, furanyl, thiazolyl, thiadiazolyl or xanthenyl.

11. The process according to claim 1 or 2, wherein said substituent R is substituted by a substituent selected from the group consisting of halogen, hydroxyl, lower alkoxy, carbamoyloxy, thio substituted by lower alkyl or a hetero ring group, lower alkylthio substituted by a hetero ring group, amino, lower alkylamino, amidiono, guanidino, acylamino, carboxy, oxycarbonyl substituted by lower alkyl, aminocarbonyl, lower alkanoyl, cyano, sulfo, lower alkyl, lower alknenyl, lower alkynyl, aryl and a heterocyclic group.

12. The process according to claim 1 or 2, wherein said carboxy protecting group $R^1$ is lower alkyl, halo-loweralkyl, lower alkoxymethyl, lower alkoxycarbonyloxy lower alkyl, lower alkanoyl lower alkyl, (5-methyl-2-oxo-1,3-dioxol -4-yl)methyl, phthalidyl, lower alkenyl, aryl lower alkyl, aryl or lower alkylsilyl.

13. The process according to claim 1 or 2, wherein said hydroxyl-protecting group $R^3$ is lower alkylsilyl, lower alkoxymethyl, tetrahydropyranyl, aralkyl, acyl, lower alkoxycarbonyl, alkenyloxycarbonyl or aralkyloxycarbonyl.

14. The process according to claim 1, wherein said compound of formula (I) is a compound of formula (I-a):

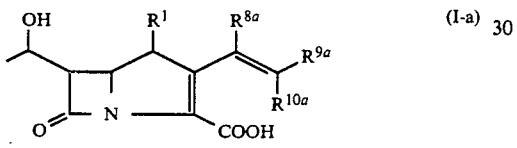

wherein $R^1$ is hydrogen or metyl and each of $R^{8a}$, $R^{9a}$ ad $R^{10a}$ is a substituent selected from the group consisting of hydrogen, lower alkyl, aminocarbonyl, lower alkoxy, cyano, lower alkoxycarbonyl and nitro, or a pharmaceutically acceptable salt or ester thereof and wherein said compound of formula (II) is a compound of formula (II-a):

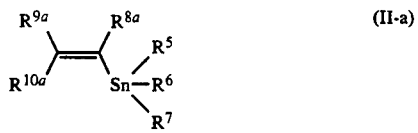

wherein each of $R^5$, $R^6$ and $R^7$ is lower alkyl and $R^{81}$, $R^{9a}$ and $R^{10a}$ are as defined above.

15. The process according to claim 2, wherein said compound of formula (I) is a compound of formula (I-a):

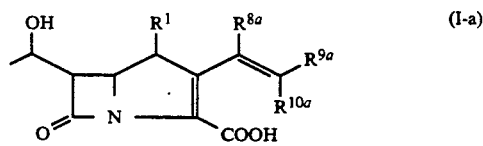

wherein $R^1$ is hydrogen or methyl and each of $R^{8a}$, $R^{9a}$ ad $R^{10a}$ is a substituent selected from he group consisting of hydrogen, lower alkyl, aminocarbonyl, lower alkoxy, cyano, lower alkoxycarbonyl and nitro, or a pharmaceutically acceptable salt or ester and wherein he compound of formula (II) is a compound of the formula (II-a):

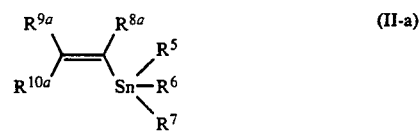

wherein each of $R^5$, $R^6$ and $R^7$ is lower alkyl and $R^{8a}$, $R^{9a}$ and $R^{10a}$ are as defined above.

16. The process according to claim 1, wherein said 2-(unsubstituted or carbon substituted)-1-carbapen-2-em-3-carboxylic acid is 4-nitrobenzyl (5R,6S)-2-(4-carbamoylphenyl)-6-((1R)-1-1-hydroxtyethyl) -1-carbapen-2-em-3-carboxylate.

* * * * *

UNITED STATES PATENT AND TRADEMARK OFFICE
CERTIFICATE OF CORRECTION

PATENT NO. : 5,258,509
DATED : November 2, 1993
INVENTOR(S) : Susumu Nakagawa et al.

It is certified that error appears in the above-indentified patent and that said Letters Patent is hereby corrected as shown below:

On the title page, Item [21],

The application number, should be: --989,510--

Signed and Sealed this

Seventeenth Day of May, 1994

Attest:

BRUCE LEHMAN

*Attesting Officer*    *Commissioner of Patents and Trademarks*